(12) United States Patent
Sutin et al.

(10) Patent No.: US 11,395,602 B2
(45) Date of Patent: Jul. 26, 2022

(54) SYSTEM AND METHOD FOR MONITORING ABSOLUTE BLOOD FLOW

(71) Applicant: The General Hospital Corporation, Boston, MA (US)

(72) Inventors: Jason Sutin, Cambridge, MA (US); Maria Angela Franceschini, Winchester, MA (US); David Boas, Winchester, MA (US)

(73) Assignee: The General Hospital Corporation, Boston, MA (US)

( * ) Notice: Subject to any disclaimer, the term of this patent is extended or adjusted under 35 U.S.C. 154(b) by 906 days.

(21) Appl. No.: 15/564,686

(22) PCT Filed: Apr. 11, 2016

(86) PCT No.: PCT/US2016/026925
§ 371 (c)(1),
(2) Date: Oct. 5, 2017

(87) PCT Pub. No.: WO2016/164894
PCT Pub. Date: Oct. 13, 2016

(65) Prior Publication Data
US 2018/0070831 A1    Mar. 15, 2018

Related U.S. Application Data

(60) Provisional application No. 62/145,087, filed on Apr. 9, 2015.

(51) Int. Cl.
*A61B 5/0205* (2006.01)
*A61B 5/026* (2006.01)
(Continued)

(52) U.S. Cl.
CPC ............ *A61B 5/031* (2013.01); *A61B 5/0075* (2013.01); *A61B 5/0205* (2013.01); *A61B 5/029* (2013.01);
(Continued)

(58) Field of Classification Search
CPC ..... A61B 5/031; A61B 5/0075; A61B 5/0205; A61B 5/0059; A61B 5/0261; A61B 5/029;
(Continued)

(56) References Cited

U.S. PATENT DOCUMENTS

2005/0015009 A1    1/2005  Mourad
2008/0004531 A1    1/2008  Carp
(Continued)

FOREIGN PATENT DOCUMENTS

CN         1044899      8/1990
CN        101720205     6/2010
(Continued)

OTHER PUBLICATIONS

Sethaput, Thunyaseth. "Mathematical Model for Hemodynamic and Intracranial Windkessel Mechanism." PhD diss., Case Western Reserve University, 2013.*
(Continued)

*Primary Examiner* — Carolyn A Pehlke
(74) *Attorney, Agent, or Firm* — Quarles & Brady LLP

(57) ABSTRACT

A system and method for non-invasively estimating an absolute blood flow of a vascular region in a subject using optical data are provided. In some aspects, the method includes acquiring optical data from the vascular region using one or more optical sensors placed about the subject, and determining, using the optical data, an index of blood flow and. a blood volume associated with the vascular region. The method also includes computing a blood inflow
(Continued)

and a blood outflow using the index of blood flow and the blood volume, and estimating an absolute blood flow using the blood inflow and blood outflow. The method further includes generating a report indicative of the absolute blood flow of the vascular region.

25 Claims, 9 Drawing Sheets

(51) Int. Cl.
| | |
|---|---|
| A61B 5/00 | (2006.01) |
| A61B 5/03 | (2006.01) |
| A61B 5/318 | (2021.01) |
| A61B 5/369 | (2021.01) |
| A61B 5/029 | (2006.01) |
| A61B 5/021 | (2006.01) |
| A61B 5/08 | (2006.01) |
| A61B 5/145 | (2006.01) |
| A61B 5/1455 | (2006.01) |

(52) U.S. Cl.
CPC ............ *A61B 5/0261* (2013.01); *A61B 5/318* (2021.01); *A61B 5/369* (2021.01); *A61B 5/6814* (2013.01); *A61B 5/7246* (2013.01); *A61B 5/7278* (2013.01); *A61B 5/021* (2013.01); *A61B 5/08* (2013.01); *A61B 5/14546* (2013.01); *A61B 5/14552* (2013.01); *A61B 2562/0238* (2013.01)

(58) Field of Classification Search
CPC ... A61B 5/0402; A61B 5/0476; A61B 5/6814; A61B 5/7246; A61B 5/7278; A61B 5/021; A61B 5/08
See application file for complete search history.

(56) References Cited

U.S. PATENT DOCUMENTS

| | | | |
|---|---|---|---|
| 2009/0062685 A1 | 3/2009 | Bergethon | |
| 2009/0149751 A1 | 6/2009 | Mourad | |
| 2010/0168586 A1 | 7/2010 | Hillman | |
| 2010/0241006 A1 | 9/2010 | Choi | |
| 2010/0268096 A1 | 10/2010 | Berka | |
| 2013/0172703 A1 | 7/2013 | Dixon | |
| 2014/0052006 A1 | 2/2014 | Lee | |
| 2014/0206980 A1* | 7/2014 | Lee | A61B 5/0261 600/407 |
| 2014/0316218 A1 | 10/2014 | Purdon | |
| 2016/0345880 A1* | 12/2016 | Nakaji | A61B 5/14546 |
| 2017/0007132 A1* | 1/2017 | Zubkov | A61B 5/0261 |

FOREIGN PATENT DOCUMENTS

| | | |
|---|---|---|
| CN | 201564473 U | 9/2010 |
| KR | 10-1008041 B1 | 1/2011 |
| WO | 2002043564 A2 | 6/2002 |
| WO | 2007097702 A1 | 8/2007 |
| WO | WO 2007097702 A1 | 8/2007 |
| WO | 2015022583 | 2/2015 |

OTHER PUBLICATIONS

Fundamental Theorem of Calculus (http://mathmistakes.info/facts/CalculusFacts/learn/doi/doi.html#:~:text=The%20conclusion%20of%20the%20fundamental%20theorem%20of%20calculus%20can%20be,undoes%20the%20result%20of%20integration%22.&text=so%20we%20see%20that%20the,)%20is%20f(x)., retrieved Oct. 18, 2020).*

Witt, Jens-Peter, Howard Yonas, and Charles Jungreis. "Cerebral blood flow response pattern during balloon test occlusion of the internal carotid artery." American journal of neuroradiology 15, No. 5 (1994): 847-856.*

Verdecchia, Kyle, Mamadou Diop, Ting-Yim Lee, and Keith St Lawrence. "Quantifying the cerebral metabolic rate of oxygen by combining diffuse correlation spectroscopy and time-resolved near-infrared spectroscopy." Journal of biomedical optics 18, No. 2 (2013): 027007.*

Brown, Derek W., Paul A. Picot, Jafar Gharavi Naeini, Roger Springett, David T. Delpy, and Ting-Yim Lee. "Quantitative near infrared spectroscopy measurement of cerebral hemodynamics in newborn piglets." Pediatric research 51, No. 5 (2002): 564-570.*

Leung, Terence S., Narendra Aladangady, Clare E. Elwell, David T. Delpy, and Kate Costeloe. "A new method for the measurement of cerebral blood volume and total circulating blood volume using near infrared spatially resolved spectroscopy and indocyanine green: application and validation in neonates." Pediatric res.*

Diop, Mamadou, Kyle Verdecchia, Ting-Yim Lee, and Keith St Lawrence. "Calibration of diffuse correlation spectroscopy with a time-resolved near-infrared technique to yield absolute cerebral blood flow measurements." Biomedical optics express 2, No. 7 (2011): 2068-2081.*

Verdecchia, K., et al. "Characterization of a hybrid diffuse correlation spectroscopy and time-resolved near-infrared spectroscopy system for real-time monitoring of cerebral blood flow and oxygenation." International Society for Optics and Photonics, 2015.*

Alali, A. S. et al. Intracranial pressure monitoring in severe traumatic brain injury: results from the American College of Surgeons Trauma Quality Improvement Program. J Neurotrauma 30, 1737-1746 (2013).

Anderson, R. C. E. et al. Complications of intracranial pressure monitoring in children with head trauma. J Neurosurg 101, 53-58 (2004).

Arridge, S. R., et al. The theoretical basis for the determination of optical pathlengths in tissue: temporal and frequency analysis. Phys Med Biol 37, 1531-1560 (1992).

Auer, LM., et al. "Effect of intracranial pressure on bridging veins in rats." Journal of neurosurgery 67.2 (1987): 263-268.

Baker, W. B. et al. Probe Pressure Modulation Algorithm Reduces Extra-cerebral Contamination in Optical Measurements of Cerebral Blood Flow. in fNIRS, Society of Functional Near-Inftared Spectroscopy (2014).

Beechem, J. M. Global analysis of biochemical and biophysical data. Meth. Enzymol. 210, 37-54 (1992).

Behrens, A. et al. Transcranial Doppler Pulsatility Index. Neurosurgery 66, 1050-1057 (2010).

Bellini, T., et al. Effects of finite laser coherence in quasielastic multiple scattering. Phys. Rev., A 44, 5215 5223 (1991).

Bellner, J. et al. Transcranial Doppler sonography pulsatility index (PI) reflects intracranial pressure (ICP). Surg Neurol 62, 45-51—discussion 51 (2004).

Binz, D. D., et al. Hemorrhagic complications of ventriculostomy placement: a meta-analysis. Neurocrit Care 10, 253-256 (2009).

Boas, D. A. et al. Haemoglobin oxygen saturation as a biomarker: the problem and a solution. Philos Transact A Math Phys Eng Sci 369, 4407-4424 (2011).

Boas, D. A. et al. Spatially varying dynamical properties of turbid media probed with diffusing temporal light correlation. JOSA A (1997).

Boas, D., et al. Scattering and Imaging with Diffusing Temporal Field Correlations. Phys Rev Lett 75, 1855-1858 (1995).

Böhmer, M., et al. "Time-resolved fluorescence correlation spectroscopy." Chemical Physics Letters 353.5-6 (2002): 439-445.

Bolognese, P., et al. Laser-Doppler flowmetry in neurosurgery. J Neurosurg Anesthesiol 5, 151-158 (1993).

Borycki, D., et al. "Interferometric Near-Infrared Spectroscopy (iNIRS) for determination of optical and dynamical properties of turbid media." Optics express 24.1 (2016): 329-354.

Buckley, E. M. et al. A Novel Combined Frequency-Domain Near-Infrared Spectroscopy and Diffuse Correlation Spectroscopy System. in Biomed BM3A.17 (OSA, 2014). doi:10.1364/BIOMED.2014.BM3A.17.

Buckley, E. M. et al. Cerebral hemodynamics in preterm infants during positional intervention measured with diffuse correlation spectroscopy and transcranial Doppler ultrasound. Opt Express 17, 12571-12581 (2009).

(56) References Cited

OTHER PUBLICATIONS

Buckley, E. M. et al. Early postoperative changes in cerebral oxygen metabolism following neonatal cardiac surgery: effects of surgical duration. J Thorac Cardiovasc Surg 145, 196-203-205.e1—discussion 203-5 (2013).
Buckley, E. M. et al. Sodium bicarbonate causes dose-dependent increases in cerebral blood flow in infants and children with single-ventricle physiology. Pediatr Res (2013). doi:10.1038/pr.2013.25.
Buckley, E. M., et al. Diffuse correlation spectroscopy for measurement of cerebral blood flow: future prospects. Neurophoton 1, 011009-011009 (2014).
Budohoski, K. P. et al. What comes first? The dynamics of cerebral oxygenation and blood flow in response to changes in arterial pressure and intracranial pressure after head injury. Br J Anaesth 108, 89-99 (2011).
Buhre, W., et al. "Extrapolation to zero-flow pressure in cerebral arteries to estimate intracranial pressure." British journal of anaesthesia 90.3 (2003): 291-295.
Burton, A. C. On the physical equilibrium of small blood vessels. Am J Physiol 164, 319-329 (1951).
Carp, S. A. et al. Due to intravascular multiple sequential scattering, Diffuse Correlation Spectroscopy of tissue primarily measures relative red blood cell motion within vessels. Biomed Opt Express 2, 2047-2054 (2011).
Carp, S. A., et al. Recovery of brain blood flow changes from diffuse correlation spectroscopy data using a layered Monte Carlo forward model. in Biomedical Optics 2014, OSA Technical Digest, Optical Society of America, 2014 (2014).
Carp, S. A., et al. Validation of diffuse correlation spectroscopy measurements of rodent cerebral blood flow with simultaneous arterial spin labeling MRI; towards MRI-optical continuous cerebral metabolic monitoring. Biomed Opt Express 1, 553-565 (2010).
Chapman, P. H., et al. The relationship between ventricular fluid pressure and body position in normal subjects and subjects with shunts: a telemetric study. Neurosurgery 26, 181-189 (1990).
Chen, J. J. et al. MRI measurement of the BOLD-specific flow-volume relationship during hypercapnia and hypocapnia in humans. Neuroimage 53, 383-391 (2010).
Cheung, C., et al. In vivo cerebrovascular measurement combining diffuse near-infrared absorption and correlation spectroscopies. Phys Med Biol 46, 2053-2065 (2001).
Chovanes, G. I. et al. The predominance of metabolic regulation of cerebral blood flow and the lack of 'Classic' autoregulation curves in the viable brain. Surg Neurol Int 3, 12 (2012).
Czosnyka, M. et al. Critical closing pressure in cerebrovascular circulation. J. Neurol. Neurosurg. Psychiatr. 66, 606-611 (1999).
Dagal, A. et al. Cerebral blood flow and the injured brain: how should we monitor and manipulate it? Current Opinion in Anaesthesiology 24, 131-137 (2011).
De Riva, N. et al. Transcranial Doppler pulsatility index: what it is and what it isn't. Neurocrit Care 17, 58-66 (2012).
Dehaes, M. et al. Cerebral oxygen metabolism in neonatal hypoxic ischemic encephalopathy during and after therapeutic hypothermia. J Cereb Blood Flow Metab 34, 87-94 (2014).
Dewey, R. C., et al. Experimental cerebral hemodynamics. Vasomotor tone, critical closing pressure, and vascular bed resistance. J Neurosurg 41, 597-606 (1974).
Dietsche, G. et al. Fiber-based multispeckle detection for time-resolved diffusing-wave spectroscopy: characterization and application to blood flow detection in deep tissue. Appl Opt 46, 8506-8514 (2007).
Diop, M., et al. Calibration of diffuse correlation spectroscopy with a time-resolved near-infrared technique to yield absolute cerebral blood flow measurements. Biomed Opt Express 2, 2068-2081 (2011).
Dong, J., et al. "Diffuse correlation spectroscopy with a fast Fourier transform-based software autocorrelator." Journal of biomedical optics 17.9 (2012): 097004.
Dong, L. et al. Noninvasive diffuse optical monitoring of head and neck tumor blood flow and oxygenation during radiation delivery. Biomed Opt Express 3, 259-272 (2012).
Durduran, T. et al. Diffuse correlation spectroscopy for non-invasive, micro-vascular cerebral blood flow measurement. Neuroimage (2013). doi:10.1016/j.neuroimage.2013.06.017.
Durduran, T. et al. Optical measurement of cerebral hemodynamics and oxygen metabolism in neonates with congenital heart defects. J Biomed Opt 15, 037004 (2010).
Durduran, T. et al. Transcranial optical monitoring of cerebrovascular hemodynamics in acute stroke patients. Opt Express 17, 3884-3902 (2009).
Durduran, T., et al. Diffuse optics for tissue monitoring and tomography. Rep Prog Phys 73, 076701 (2010).
Early, C. B., et al. Dynamic pressure-flow relationships of brain blood flow in the monkey. J Neurosurg 41, 590-596 (1974).
Edwards, A. D. et al. Cotside measurement of cerebral blood flow in ill newborn infants by near infrared spectroscopy. Lancet 2, 770-771 (1988).
Eggeling, C. et al. Data registration and selective single-molecule analysis using multi-parameter fluorescence detection. J. Biotechnol. 86, 163-180 (2001).
Eid, J. S., et al. Data acquisition card for fluctuation correlation spectroscopy allowing full access to the detected photon sequence. Rev Sci Instrum 71, 361 (2000).
Favilla, C. G. et al. Optical bedside monitoring of cerebral blood flow in acute ischemic stroke patients during head-of-bed manipulation. Stroke 45, 1269-1274 (2014).
Franceschini, M. A. et al. Near-infrared spiroximetry: noninvasive measurements of venous saturation in piglets and human subjects. J Appl Physiol 92, 372-384 (2002).
Franceschini, M. A. et al. The effect of different anesthetics on neurovascular coupling. Neuroimage 51, 1367-1377 (2010).
Franceschini, M. A., et al. Noninvasive optical method of measuring tissue and arterial saturation: an application to absolute pulse oximetry of the brain. Opt Lett 24, 829-831 (1999).
Gagnon, L. et al. Double-layer estimation of intra- and extracerebral hemoglobin concentration with a time-resolved system. J Biomed Opt 13, 054019 (2008).
Grubb, R. L., et al. The effects of changes in PaCO2 on cerebral blood volume blood flow, and vascular mean transit time. Stroke 5, 630-639 (1974).
Guarracino, F. Cerebral monitoring during cardiovascular surgery. Current Opinion in Anaesthesiology 21, 50-54 (2008).
Guillaume, J. et al. [Continuous intracranial manometry; importance of the method and first results]. Rev. Neurol. (Paris) 84, 131-142 (1951).
Gurley, K. et al. "Noninvasive optical quantification of absolute blood flow, blood oxygenation, and oxygen consumption rate in exercising skeletal muscle." Journal of biomedical optics 17.7 (2012): 075010.
Holloway, K. L. et al. Ventriculostomy infections: the effect of monitoring duration and catheter exchange in 584 patients. J Neurosurg 85, 419-424 (1996).
Ijichi, S. et al. Developmental changes of optical properties in neonates determined by near-infrared time-resolved spectroscopy. Pediatr Res 58, 568-573 (2005).
International Search Report and Written Opinion for International Application No. PCT/US2016/026925 dated Jul. 6, 2016, 11 pages.
Irwin, D. et al. Influences of tissue absorption and scattering on diffuse correlation spectroscopy blood flow measurements. Biomed Opt Express 2, 1969-1985 (2011).
Ito, H., et al. Changes in human cerebral blood flow and cerebral blood volume during hypercapnia and hypocapnia measured by positron emission tomography. J Cereb Blood Flow Metab 23, 665-670 (2003).
Jain, V. et al. Cerebral oxygen metabolism in neonates with congenital heart disease quantified by MRI and optics. J Cereb Blood Flow Metab (2013). doi:10.1038/jcbfm.2013.214.
Jiang, L., et al. High-power DBR laser diodes grown in a single epitaxial step. in SPIE OPTO: Integrated Optoelectronic Devices (Belyanin, A. A. & Smowton, P. M.) 7230, 72301F-72301F-9 (SPIE, 2009).

(56) References Cited

OTHER PUBLICATIONS

Jones, M., et al. Changes in blood flow, oxygenation, and volume following extended stimulation of rodent barrel cortex. Neuroimage 15, 474-487 (2002).
Kangara, J. C. B. et al. Design and construction of cost-effective tapered amplifier systems for laser cooling and trapping experiments. Am. J. Phys. 82, 805-817 (2014).
Kienle, A. et al. Improved solutions of the steady-state and the time-resolved diffusion equations for reflectance from a semi-infinite turbid medium. J Opt Soc Am A 14, 246-254 (1997).
Kim, M. N. et al. Continuous Optical Monitoring of Cerebral Hemodynamics During Head-of-Bed Manipulation in Brain-Injured Adults. Neurocrit Care (2013). doi:10.1007/s12028-013-9849-7.
Kim, M. N. et al. Noninvasive measurement of cerebral blood flow and blood oxygenation using near-infrared and diffuse correlation spectroscopies in critically brain-injured adults. Neurocrit Care 12, 173-180 (2010).
Kirkpatrick, P. J., et al. Continuous monitoring of cortical perfusion by laser Doppler flowmetry in ventilated patients with head injury. J. Neurol. Neurosurg. Psychiatr. 57, 1382-1388 (1994).
Kirkpatrick, PJ, et al. "Near-infrared spectroscopy use in patients with head injury." Journal of neurosurgery 83.6 (1995): 963-970.
Klingelhöfer, J. et al. Doppler CO2 test as an indicator of cerebral vasoreactivity and prognosis in severe intracranial hemorrhages. Stroke 23, 962-966 (1992).
Li, J., et al. "Pulsation-resolved deep tissue dynamics measured with diffusing-wave spectroscopy." Optics express 14.17 (2006): 7841-7851.
Li, Z., et al. "Calibration of diffuse correlation spectroscopy blood flow index with venous-occlusion diffuse optical spectroscopy in skeletal muscle." Journal of biomedical optics 20.12 (2015): 125005.
Liebert, A. et al. Evaluation of optical properties of highly scattering media by moments of distributions of times of flight of photons. Appl Opt 42, 5785-5792 (2003).
Liebert, A., et al. Fiber dispersion in time domain measurements compromising the accuracy of determination of optical properties of strongly scattering media. J Biomed Opt 8, 512-516 (2003).
Lin, P.-Y. et al. Non-invasive optical measurement of cerebral metabolism and hemodynamics in infants. J Vis Exp e24379 (2013). doi:10.3791/4379.
Lin, P.-Y. et al. Regional and hemispheric asymmetries of cerebral hemodynamic and oxygen metabolism in newborns. Cereb Cortex 23, 339-348 (2013).
Lynch, J. M. et al. Noninvasive optical quantification of cerebral venous oxygen saturation in humans. Acad Radiol 21, 162-167 (2014).
Maas, A. I. R., et al. Moderate and severe traumatic brain injury in adults. Lancet Neurol 7, 728-741 (2008).
Magatti, D. et al. "Fast multi-tau real-time software correlator for dynamic light scattering." Applied optics 40.24 (2001): 4011-4021.
Marzban, C. et al. A method for estimating zero-flow pressure and intracranial pressure. J Neurosurg Anesthesiol 25, 25-32 (2013).
Matcher, S. J., et al. In vivo measurements of the wavelength dependence of tissue-scattering coefficients between 760 and 900 nm measured with time-resolved spectroscopy. Appl Opt 36, 386-396 (1997).
Mesquita, R. C. et al. Direct measurement of tissue blood flow and metabolism with diffuse optics. Philos Transact A Math Phys Eng Sci 369, 4390-4406 (2011).
Mesquita, R. C. et al. Influence of probe pressure on the diffuse correlation spectroscopy blood flow signal: extra-cerebral contributions. Biomed Opt Express 4, 978-994 (2013).
Muehlschlegel, S. et al. Feasibility of NIRS in the neurointensive care unit: a pilot study in stroke using physiological oscillations. Neurocrit Care 11, 288-295 (2009).
Naqvi, J., et al. Transcranial Doppler ultrasound: a review of the physical principles and major applications in critical care. Int J Vasc Med 2013, 629378 (2013).
Ninck, M. et al. "Diffusing-wave spectroscopy with dynamic contrast variation: disentangling the effects of blood flow and extravascular tissue shearing on signals from deep tissue." Biomedical optics express 1.5 (2010): 1502-1513.
Ono, M., et al. Validation of a stand-alone near-infrared spectroscopy system for monitoring cerebral autoregulation during cardiac surgery. Anesth Analg 116, 198-204 (2013).
Panerai, R. B. The critical closing pressure of the cerebral circulation. Med Eng Phys 25, 621-632 (2003).
Patel, J., et al. Measurement of cerebral blood flow in newborn infants using near infrared spectroscopy with indocyanine green. Pediatr Res 43, 34-39 (1998).
Patterson, M. S., et al. Time resolved reflectance and transmittance for the non-invasive measurement of tissue optical properties. Appl Opt 28, 2331-2336 (1989).
Phillip, D. et al. Altered Low Frequency Oscillations of Cortical Vessels in Patients with Cerebrovascular Occlusive Disease—A NIRS Study. Front Neurol 4, 204 (2013).
Phillip, D. et al. Low frequency oscillations in cephalic vessels assessed by near infrared spectroscopy. Eur. J. Clin. Invest. 42, 1180-1188 (2012).
Pifferi, A. et al. Time-resolved diffuse reflectance using small source-detector separation and fast single-photon gating. Phys Rev Lett 100, 138101 (2008).
Poelker, M. High power gain-switched diode laser master oscillator and amplifier. Appl Phys Lett (1995).
Poulin, M. J., et al. Dynamics of the cerebral blood flow response to step changes in end-tidal PCO2 and PO2 in humans. J Appl Physiol 81, 1084-1095 (1996).
Robertson, C. S. Management of Cerebral Perfusion Pressure after Traumatic Brain Injury. Anesthesiology 95, 1513 (2001).
Roche-Labarbe, N. et al. Near-infrared spectroscopy assessment of cerebral oxygen metabolism in the developing premature brain. J Cereb Blood Flow Metab 32, 481-488 (2012).
Roche-Labarbe, N. et al. Noninvasive optical measures of CBV, StO(2), CBF index, and rCMRO(2) in human premature neonates' brains in the first six weeks of life. Hum Brain Mapp 31, 341-352 (2010).
Roche-Labarbe, N. et al. Somatosensory evoked changes in cerebral oxygen consumption measured non-invasively in premature neonates. Neuroimage (2013). doi:10.1016/j.neuroimage.2013.01.035.
Roche-Labarbe, N., et al. Assessment of Infant Brain Development. (Wiley-VCH, 2011).
Rowney, D. A., et al. Cerebrovascular carbon dioxide reactivity in children anaesthetized with sevoflurane. Br J Anaesth 88, 357-361 (2002).
Selb, J. et al. Sensitivity of near-infrared spectroscopy and diffuse correlation spectroscopy to brain hemodynamics simulations and experimental findings during hypercapnia. Neurophoton 1, (2014).
Selb, J., et al. Comparison of a layered slab and an atlas head model for Monte Carlo fitting of time-domain near-infrared spectroscopy data of the adult head. J Biomed Opt 19, 16010 (2014).
Selb, J., et al. Improved sensitivity to cerebral hemodynamics during brain activation with a time-gated optical system: analytical model and experimental validation. J Biomed Opt 10, 11013 (2005).
Selb, J., et al. Sensitivity of Continuous-Wave NIRS and Diffuse Correlation Spectroscopy to Cerebral Hemodynamics during Hypercapnia. in Biomedical Optics 2014, OSA Technical Digest, Optical Society of America, 2014 BT5B.6. (2014).
Selb, J., et al. Time-gated optical system for depth-resolved functional brain imaging. J Biomed Opt 11, 044008 (2006).
Shang, Y. et al. Cerebral monitoring during carotid endarterectomy using near-infrared diffuse optical spectroscopies and electroencephalogram. Phys Med Biol 56, 3015-3032 (2011).
Smith, M. Monitoring Intracranial Pressure in Traumatic Brain Injury. Anesth Analg 106, 240-248 (2008).
Stein, S. C., et al. Relationship of aggressive monitoring and treatment to improved outcomes in severe traumatic brain injury. J Neurosurg 112, 1105-1112 (2010).
Steiner, L. A. et al. Monitoring the injured brain: ICP and CBF. Br J Anaesth 97, 26-38 (2006).
Steiner, L. A. et al. Near-infrared spectroscopy can monitor dynamic cerebral autoregulation in adults. Neurocrit Care 10, 122-128 (2009).

(56) References Cited

OTHER PUBLICATIONS

Thees, C. et al. Relationship between intracranial pressure and critical closing pressure in patients with neurotrauma. Anesthesiology 96, 595-599 (2002).
Themelis, G. et al. Near-infrared spectroscopy measurement of the pulsatile component of cerebral blood flow and volume from arterial oscillations. J Biomed Opt 12, 014033 (2007).
Torricelli, A., et al. "Time domain functional NIRS imaging for human brain mapping." Neuroimage 85 (2014): 28-50.
Torricelli, A., et al. In vivo optical characterization of human tissues from 610 to 1010 nm by time-resolved reflectance spectroscopy. Phys Med Biol 46, 2227-2237 (2001).
Ursino, M. et al. A mathematical model of the relationship between cerebral blood volume and intracranial pressure changes: the generation of plateau waves. Ann Biomed Eng 19, 15-42 (1991).
Ursino, M. et al. A simple mathematical model of the interaction between intracranial pressure and cerebral hemodynamics. J Appl Physiol 82, 1256-1269 (1997).
Ursino, M., et al. Intracranial pressure dynamics in patients with acute brain damage: a critical analysis with the aid of a mathematical model. IEEE Trans Biomed Eng 42, 529-540 (1995).
Vajkoczy, P. et al. Continuous monitoring of regional cerebral blood flow: experimental and clinical validation of a novel thermal diffusion microprobe. J Neurosurg 93, 265-274 (2000).
Varsos, G. V. et al. Critical closing pressure determined with a model of cerebrovascular impedance. J Cereb Blood Flow Metab 33, 235-243 (2013).
Verdecchia, K., et al. "Quantifying the cerebral metabolic rate of oxygen by combining diffuse correlation spectroscopy and time-resolved near-infrared spectroscopy." Journal of biomedical optics 18.2 (2013): 027007.
Verdecchia, K., et al. Multi-Distance Depth-Resolved Diffuse Correlation Spectroscopy, in Biomedical Optics 2014, OSA Technical Digest, Optical Society of America, 2014 (2014).
Wagner, B. P. et al. Dynamic cerebral autoregulatory response to blood pressure rise measured by near-infrared spectroscopy and intracranial pressure. Crit. Care Med 30, 2014 (2002).
Weerakkody, R. A. et al. Slow vasogenic fluctuations of intracranial pressure and cerebral near infrared spectroscopy—an observational study. Acta Neurochir 152, 1763-1769 (2010).
Williams, M. et al. Intraoperative blood pressure and cerebral perfusion: strategies to clarify hemodynamic goals. Paediatr Anaesth 24, 657-667 (2014).
Yodh, A. G., et al. "Pulsed diffusing-wave spectroscopy: High resolution through nonlinear optical gating." Physical review B 42.7 (1990): 4744.
Yu, G. et al. Validation of diffuse correlation spectroscopy for muscle blood flow with concurrent arterial spin labeled perfusion MRI. Opt Express 15, 1064-1075 (2007).
Yücel, M. A. et al. Validation of the hypercapnic calibrated fMRI method using DOT-fMRI fusion imaging. Neuroimage (2014). doi:10.1016/j.neuroimage.2014.08.052.
Yücel, M. A., et al. Reducing motion artifacts for long-term clinical NIRS monitoring using collodion-fixed prism-based optical fibers. Neuroimage 85 Pt 1, 192-201 (2014).
Zhou, C. et al. Diffuse optical monitoring of hemodynamic changes in piglet brain with closed head injury. J Biomed Opt 14, 034015 (2009).
Zirak, P. et al. Transcranial diffuse optical monitoring of microvascular cerebral hemodynamics after thrombolysis in schemic stroke. J Biomed Opt 19, 18002 (2014).
Zirak, P., et al. Microvascular versus macrovascular cerebral vasomotor reactivity in patients with severe internal carotid artery stenosis or occlusion. Acad Radiol 21, 168-174 (2014).
Zuluaga, M. T., et al. "Diagnosis Influences Response of Cerebral NIRS to Intracranial Hypertension in Children." Pediatric critical care medicine: a journal of the Society of Critical Care Medicine and the World Federation of Pediatric Intensive and Critical Care Societies 11.4 (2010): 514.
Varsos, G. V., et al. "Critical closing pressure during intracranial pressure plateau waves." Neurocritical care 18.3 (2013): 341-348.
China National Intellectual Property Administration, Notice on the First Office Action for application 201680032216.3. dated Mar. 16, 2020.
Japan Patent Office. Notification of Reasons for Refusal for application 2017-552841. dated Aug. 25, 2020. With translation. 6 pages.
Japan Patent Office. Decision to grant patent for application 2017-552841. dated Jan. 12, 2021. With translation. 5 pages.
China National Intellectual Property Administration, Notice on the Second Office Action for application 201680032216.3. dated Jan. 25, 2021. With translation. 18 pages.
Japan Patent Office. Notification of Reasons for Refusal for application 2017-552842. dated Jan. 16, 2020. With translation. 8 pages.
Japan Patent Office. Decision to grant patent for application 2017-552842. dated Oct. 6, 2020. With translation. 5 pages.
Japan Patent Office. Notification of Reasons for Refusal for application 2017-552842. dated Jun. 2, 2020. With translation. 6 pages.
China National Intellectual Property Administration, Text on the Decision on Rejection for application 201680032216.3. dated Dec. 24, 2021. With translation. 18 pages.
China National Intellectual Property Administration, Notice on the Third Office Action for application 201680032216.3. dated May 20, 2021. With translation. 13 pages.

* cited by examiner

SYSTEM AND METHOD FOR MONITORING ABSOLUTE BLOOD FLOW

CROSS-REFERENCE TO RELATED APPLICATIONS

This application is a U.S. National Phase of PCT Application No. PCT/US2016/026925 filed on Apr. 11, 2016 which is based on, claims the benefit of, and incorporates herein in its entirety, U.S. Provisional Patent Application Ser. No. 62/145,087 filed on Apr. 9, 2015, and entitled "SYSTEMS AND METHODS FOR MEASURING TISSUE PRESSURE."

STATEMENT REGARDING FEDERALLY SPONSORED RESEARCH

This invention was made with government support under P41-EB015896, R01-HD042908, and R01-EB001954 awarded by the National Institutes of Health. The government has certain rights in the invention.

BACKGROUND

The disclosure relates generally to systems and methods for measuring tissue properties. More particularly, the disclosure is directed to systems and methods for determining absolute blood flow non-invasively using physiological measurements.

Physiological monitoring of oxygen consumption by organs as well as deliverance of oxygen through blood flow has great significance for many applications, including healthcare, rehabilitation, performance monitoring, and athletic training. For instance, cerebral monitoring can provide significant improvement in the management of patients with brain injury, patients at risk for brain injury, and patients undergoing routine general anesthesia and surgical procedures that alter cerebral oxygen delivery.

Near-infrared spectroscopy (NIRS) has been used for more than two decades to monitor tissue oxygenation ($SO_2$) as a surrogate of blood flow (BF) and oxygen delivery. While NIRS oximeters show significant correlation between $SO_2$ and arterial blood pressure, oxygenation is not the same as blood flow or metabolism. The $SO_2$—BF relationship is affected by changes in oxygen consumption (i.e. the metabolic rate of oxygen, $MRO_2$), arterial oxygenation ($SaO_2$), hemoglobin in the blood (HGB), and in the relative volumes of the arterial and venous compartments. It is therefore highly desirable to measure blood flow in tissues, either alone, or in combination with a measurement of oxygenation. Furthermore, it is desirable for these measurements to be made in a continual or continuous manner to enable applications such as monitoring during intensive care or in the field. It is also highly desirable for these measurements to be made non-invasively, for example with an instrument probe external to the body for measuring blood flow or blood flow and oxygenation of an internal organ with minimal influence from overlying layers of skin, muscle, and/or bone, or minimally invasive, for example with a laparoscope or endoscope.

Although various methods for quantitatively measuring blood flow have been utilized, most are either invasive and/or non-continuous. Modern techniques for measuring cerebral blood flow in humans include radiographic clearance methods, magnetic resonance imaging (MRI) spin-labeling, transcranial Doppler ultrasound (TCD), thermal diffusion, and laser Doppler flowmetry (LDF).

Radiographic clearance methods are the oldest techniques and generally involve measuring the rate of washout of a radioisotope tracer. Radiographic methods have the advantage of quantitatively measuring absolute regional blood flow throughout the entire brain, including deep brain structures. However, they have the disadvantages of requiring radiation, being expensive and slow, and cannot be performed continuously or at the bed-side or in the field. MRI arterial spin-labeling (ASL) is another non-invasive method to measure regional blood flow throughout the entire brain. However, the accuracy and precision of the method is poor, quantitation is difficult, and the dynamic range of measurable flow rates are limited by the lifetime of the spin label. As with radiographic methods, ASL cannot be deployed at the bedside or in the field.

Transcranial Doppler ultrasound measures cerebral blood flow velocity in large cerebral arteries as a surrogate for global cerebral blood flow. While TCD is non-invasive, it cannot provide regional measures of microcirculation and is confounded by changes in vessel caliber. TCD also requires significant expertise for proper use, and is difficult to apply continuously for extended periods of time as the ultrasonic probe must be maintained in a proper orientation with the insonated cerebral artery. TCD also has difficulty measuring flow velocity in the anterior cerebral arterial which supplies blood to the clinically important frontal region of the brain. Finally, due to normal anatomical variations, skull thickness in about 15% of subjects is too thick to allow blood flow measurements by TCD.

The most clinically used invasive measures of cerebral blood flow (CBF) are thermal diffusion flowmetry and laser Doppler flowmetry. Specifically, thermal diffusion flowmetry measures absolute blood flow in a small region localized around a thermal diffusion probe fitted with a heated thermistor. To measure CBF, the probe is inserted a few centimeters into the brain. The power dissipated by the thermistor is then utilized to provide a measurement for CBF.

Laser Doppler flowmetry is similarly invasive, requiring a hole burred through the skull and a probe placed directly on the surface of the brain itself. Since the LDF detection volume is small (~1 $mm^3$), LDF flow values are highly variable, with values dependent on slight differences in the local vascular anatomy underneath the probe and not necessarily representative of the microcirculation of the tissue of interest. LDF has the further disadvantage of not being calibrated to absolute flow.

Typically in LDF, a long coherence length source of light illuminates the specimen and backscattered light is measured from a location in the immediate vicinity of the location where the illumination is directed onto the sample. For example, a common LDF configuration uses a multi-modal optical fiber to deliver light to the subject and a second multi-mode fiber, laterally displaced about 0.25 mm from the source fiber, to receive light transmitted from the source through the tissue. Other configurations use free space or single-mode optical fibers or a combination of fiber optics and free-space. Regardless of the means of delivering and detecting light, the close proximity of the light source and detectors has the advantage of increasing the flux of light at the detector, since the intensity of the scattered light decreases roughly exponentially with distance from the illumination source. Furthermore, the short distances increase the coherence area at the detector, allowing the use of more efficient multimode detectors. Thus, in LFD a relatively large amount of light is detected and analog detection schemes are typically employed. Light scattering from particles moving in the specimen introduces a detectable flow-dependent Doppler broadening to the scattered light. Although, the optical spectra of the scattered light could be measured directly, fluctuations in the detected intensity are more commonly measured. The temporal power spectrum or auto correlation is then computed to quantify the dynamic scattering. Typically, LDF is realized in the single or few scattering regime and often simple moment analysis is used to quantify flow.

While thermal diffusion flowmetry and LDF can provide continuous measurements, the invasiveness of these techniques clearly limit their application to severely ill patients, or patients undergoing invasive procedures.

Diffuse correlation spectroscopy (DCS), on the other hand, is non-invasive optical measurement technique. In contrast to LDF, DCS is realized in the multiply scattering regime that enables measurement of deep tissues. In DCS, source-detector separations are typically more than a hundred-fold greater than the separations used in LDF. The depth of sensitivity of the measurement into the tissue is roughly approximately half the source detector separation distance, so 3 cm separations are typically adequate for a non-invasive transcranial measurement of cerebral blood flow in adults. Thus, DCS is an improvement over LDF because DCS enables non-invasive measurement of cerebral perfusion. Another advantage of DCS is that its larger sensitive area provides greater spatial averaging over the tissue region of interest, leading improved robustness of the flow measurement compared to LDF.

To quantify blood flow in a tissue of interest using DCS, a blood flow index (BFi) is usually computed based on intensity autocorrelation functions obtained from the detected light intensities. Specifically, generated autocorrelation functions are fit to a correlation transport model from which the BFi is extracted. However, at present, quantitative absolute measurements of blood flow, which is related to BFi, are difficult to obtain. Therefore, more common approaches utilize a relative blood flow (rBF), which quantifies blood flow changes relative to a baseline. As such, cerebral blood flow is typically quantified in terms of a relative cerebral blood flow (rCBF).

Previous attempts to measure absolute blood flow, which includes the inflow and outflow of blood from a tissue of interest, have been aimed at calibrating DCS measurements against a measure of absolute flow obtained. In particular, BFi measurements have been calibrated against changes in total hemoglobin concentration. The latter provides an inflow of hemoglobin in units of concentration per unit time, which when divided by the blood hemoglobin concentration (i.e. hematocrit), can give a volume of blood per unit time, which is indicative absolute flow. However, these methods require complete occlusion of venous outflow of blood, which can only be obtained by applying pressures cuffs or other devices that modify or restrict normal physiological flow conditions. Furthermore, as may appreciated, such approaches are also limited to measurement of body extremities, such as arms or legs, since using devices that obstruct blood flow to the brain is not advised due to safety concerns.

Consequently, considering the limitations of previous technological approaches, systems and methods capable of non-invasively, continuously and accurately measuring absolute blood flow, including absolute cerebral blood flow, are highly desirable.

SUMMARY

The present disclosure overcomes the aforementioned drawbacks by providing a system and method for accurately, non-invasively and continuously monitoring patients. More specifically, the system and method described herein utilizes optical measurements, including diffuse correlation spectroscopy (DCS) measurements, to estimate absolute blood flow, and other quantities.

In one aspect of the disclosure, a system for non-invasively monitoring absolute blood flow of a vascular region in a subject using optical data is provided. The system includes an optical coupling system configured to transmit to and receive light signals from one or more locations about a subject, and an optical processing system configured to generate optical data using received light signals. The system also includes a computer programmed to receive, from the optical processing system, optical data associated with a vascular region, and determine, using the optical data, an index of blood flow and a blood volume. The computer is also programmed to compute a blood inflow and a blood outflow using the index of blood flow and the blood volume, and estimate an absolute blood flow using the blood inflow and blood outflow. The computer is further programmed to generate a report indicative of the absolute blood flow of the vascular region.

In another aspect of the disclosure, a method for non-invasively estimating an absolute blood flow of a vascular region in a subject using optical data is provided. In some aspects, the method includes acquiring optical data from the vascular region using one or more optical sensors placed about the subject, and determining, using the optical data, an index of blood flow and a blood volume associated with the vascular region. The method also includes computing a blood inflow and a blood outflow using the index of blood flow and the blood volume, and estimating an absolute blood flow using the blood inflow and blood outflow. The method further includes generating a report indicative of the absolute blood flow of the vascular region.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

Blood flow or tissue perfusion monitoring is important for the diagnosis and treatment of patients with a wide range of medical conditions and disorders, including traumatic brain injury, intracerebral and subarachnoid hemorrhage, hydrocephalus, benign intracranial hypertension, meningitis, stroke, acute liver failure, and so forth. In some cases, it is highly desirable to absolutely quantify blood flow in order to provide accurate comparison from subject to subject, so that normative blood flow levels can be defined and thresholds established for clinical intervention, for example.

Therefore, in accordance with aspects of the present disclosure, a system and a method for accurate, non-invasive monitoring of blood flow, including cerebral blood flow, are described herein. In particular, the provided system and method utilize optical measurements, including diffuse correlation spectroscopy (DCS) measurements, to estimate absolute blood flow. In some aspects, optical data may advantageously generated at a temporal resolution greater than a pulsatile frequency of a cardiac cycle. As a result, pulsatile blood flow measurements can be obtained to determine an absolute blood flow.

Herein, blood flow may also refer to perfusion, tissue perfusion, and the like. Therefore, an absolute blood flow may refer to an absolute perfusion, or an absolute tissue perfusion. Also, although the disclosure makes reference to cerebral blood flow, one of ordinary skill will readily appreciate that the following discussion is not limited to blood flow in cerebral tissues, and can indeed be applicable to other organs and tissues, including organs and tissues associated with the neck, arms, hands, fingers, torso, chest, legs, feet, toes, and elsewhere.

As will be described, the present approach may not only provide valuable blood flow information, on a continuous basis, for administering acute care at a patient bedside or in an ambulance, but can also provide information for analyzing complex pathophysiology, identifying new therapeutic opportunities, and, in general, substantially improving neurocritical care management. In some applications, the present approach may be used in the diagnosis, monitoring and treatment of traumatic brain injury or concussions, as other cardiovascular conditions. Also, in addition to human monitoring, the present system and method may also be with animal subjects for research, commercial, and veterinary purposes.

Figure 1:
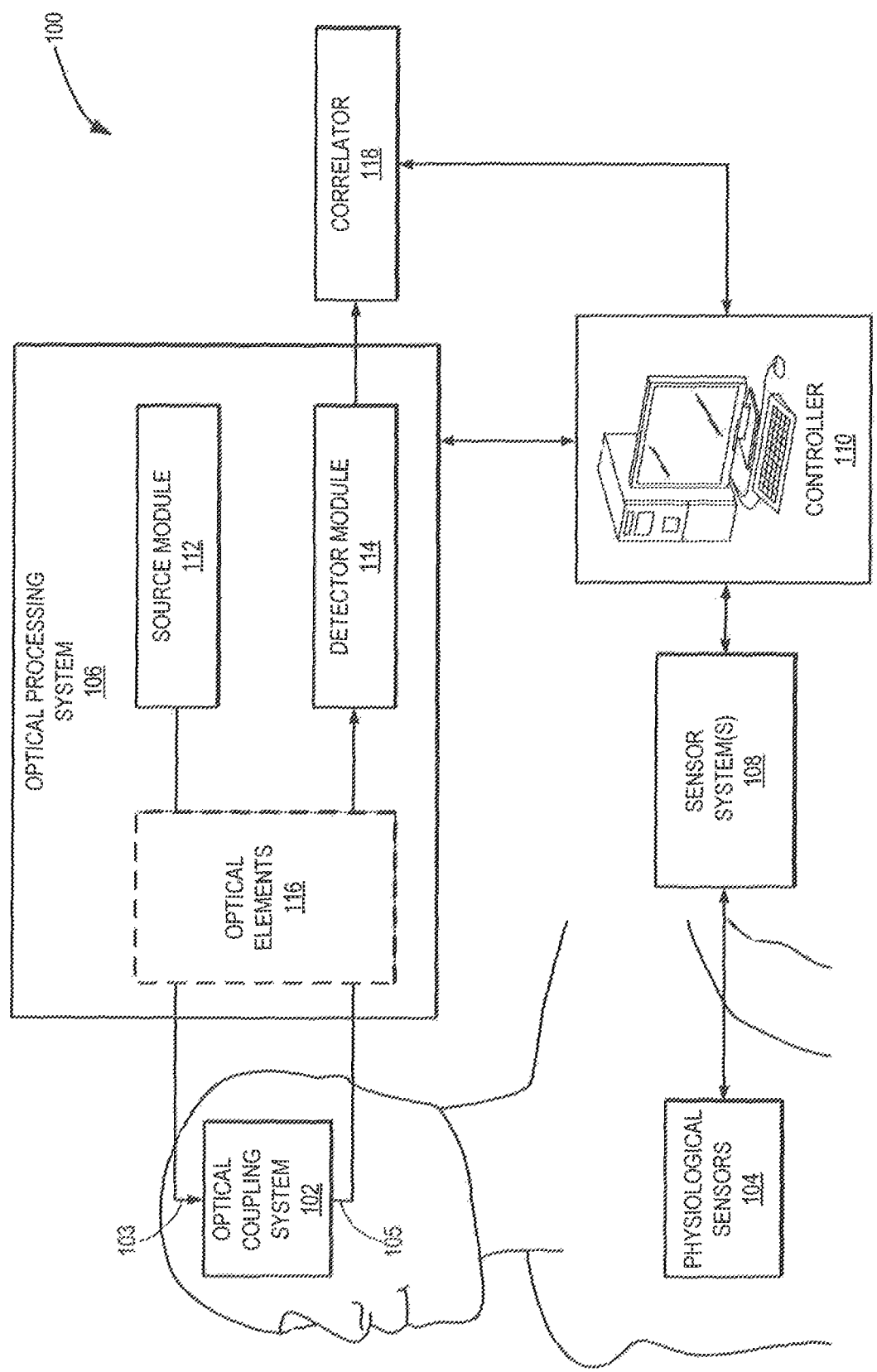
FIG. 1 a diagram of an example monitoring system, in accordance with aspects of the present disclosure.

Turning to FIG. 1, a block diagram is shown of an exemplary system 100 for non-invasive monitoring of a subject, in accordance with aspects of the present disclosure. As shown, the system 100 generally includes a number of sensors, including an optical coupling system 102 and physiological sensors 104, to be placed at various locations about a subject's body. The system 100 also includes an optical processing system 106 and one or more sensor system(s) 108 in communication with the physiological sensors 104. The optical processing system 106 and sensor system(s) 108 are in communication with a controller 110 that is configured control operation of the system 100, and systems therein, including data acquisition and processing.

The system 100 may operate autonomously or semi-autonomously, or in conjunction with other devices or hardware. The system 600 may also read executable software instructions from a non-transitory computer-readable medium (such as a hard drive, a CD-ROM, flash memory and the like), and may also receive instructions from a user, or any other source logically connected thereto, such as another networked computer or server, database, internet, cloud, and so forth.

The optical coupling system 102 may include a number of source probes 103 and detector probes 105 forming one or more optical sensors, including DCS sensors, and near infra-red spectroscopy (NIRS) sensors. In particular, the source probes 103 are configured to transmit light signals to the subject, while the detector probes 105 are configured to receive light signals therefrom. The source probes 103 and detector probes 105 can include single-mode and/or multi-mode optical fibers. The optical fibers may be straight fibers, 90° bent fibers, or side-firing fibers. The source probes 103 and detector probes 105 may be arranged in various configurations and separated by distances up to several centimeters. In some implementations, the optical coupling system 102 is configured for measuring blood flow in the brain, and optionally, blood flow in the skin, scalp, skull, and/or periphery.

The physiological sensors 104, controlled by the sensor systems(s) 108, may include electroencephalogram (EEG), electrocardiograph (ECG), blood pressure (BP), pulse oxymetry, and other sensors, configured to measure physiological parameters, including, but not limited to, hemoglobin concentrations, changes in hemoglobin concentrations, oxygen saturation, $CMRO_2$, invasive blood pressure, non-invasive blood pressure, intracranial pressure, brain activity, electrocardiogram, cardiac output, stroke volume, and combinations thereof. In some implementations, physiological sensors 104 and respective sensor system(s) 108 may be from a separate device from a different manufacturer.

Various sensors described with reference to the optical coupling system 102 and physiological sensors 104 may be incorporated into, or be part of, one or more items or units designed to engage with or couple to a subject at any number of locations, in any number of geometrical configurations. For example, various sensors may be integrated into silicone assemblies, bandages, headbands, and any other assemblies securable to the subject. Also, various sensors may be wearable or designed to attach to the subject directly using an adhesive.

Although FIG. 1 shows the optical coupling system 102 placed about a subject's head, and physiological sensors 104 placed about the subject's torso, it may be readily appreciated that the locations of the sensors can vary, in accordance with the signals being induced and sensed. For example, various physiological sensors 104 may be placed about the subject's head, arms, legs, and so forth. Similarly, optical sensors may be placed about the subject's arms, legs, torso, and so forth. As such, different sensors may be collocated, or individually placed at various positions about the subject.

The optical processing system 106 is in communication with the optical coupling system 102 includes a source module 112 configured to generate light using one or more light sources. The source module 112 may be configured to operate in the continuous wave, frequency domain, and time domain. To this end, the source module 112 may be pulsed, sinusoidally modulated, step modulated, triangularly modulated, and/or arbitrarily modulated.

By way of example, the source module 112 may include a transform, or nearly-transform, limited picosecond pulsed source or a non-transform limited picoseconds pulsed source. As used herein, reference to "picosecond" pulses or pulsed source refers to pulses having a pulse width between 1 ps and 10 ns. The source module 112 may also include a Bragg reflector laser, a distributed Bragg feedback laser, a gain-switched distributed Bragg reflector laser, an external cavity laser, a gain-switched laser, a current pulsed laser, a mode-locked laser, a q-switched laser, combinations thereof, and the like. The source module 112 can also include a diode laser, a solid-state laser, a fiber laser, a vertical cavity surface-emitting laser (VCSEL), a Fabry-Perot laser, a ridge laser, a ridge waveguide laser, a tapered laser, a master oscillator power amplifier (MOPA) laser, or other type of laser. In certain aspects, the source module 112 can also include a swept source light source.

The source module 112 can be configured to transmit light into a target medium using wavelengths between 400 nm and 1500 nm, including but not limited to, a wavelength of between 600 nm and 1000 nm, or a wavelength of between 690 nm and 900 nm. The source module 112 can also be configured to transmit light into the target medium using average power between 10 µW and 10 W, including but not limited to, an average power of between 100 µW and 1 W, between 1 mW and 500 mW, or between 10 mW and 200 mW. The source module 112 can be configured to transmit light pulses into a target medium using pulse widths between 1 ps and 10 ns, including but not limited to, a pulse width of between 10 ps and 1 ns, or between 50 ps and 500 ps. Pulse widths described herein refer to full-width at half maximum pulse widths.

The optical processing system 106 also includes a detector module 114 in communication with the optical coupling system 102 which is configured to receive light signals from the subject and provide an output to a correlator 118 indicative of the received signals. For example, the detector module 114 may include one or more photon-counting avalanche photodiodes (APDs) configured to provide photon counts based on detected light. As shown in FIG. 1, the optical processing system 106 may optionally include a number of optical elements 116 interposed between the optical coupling system 102, source module 112 and detector module 114. Specifically, the optical elements 116 may be configured for manipulating light signals transmitted to and received from the subject. Example optical elements 116 include lenses, prisms, holograms or diffractive optical elements, diffusers, attenuators, filters, optical fibers, and so forth.

In general, the controller 110 may be a computer, as shown in FIG. 1, that is programmed to carry out steps in accordance with aspects of the present disclosure, as will be described. The controller 110 may also be a workstation, a laptop, a mobile device, a tablet, a personal digital assistant (PDA), a multimedia device, a network server, a mainframe or any other general-purpose or application-specific computing device. Other examples for the controller 110 may also include system on a chip (SOC) a field-programmable gate array (FPGA), a complex programmable logic device (CPLD), an application-specific integrated circuit (ASIC), a Raspberry PI controller, and the like.

In some aspects, the controller 110 may be configured to direct the acquisition and processing of optical, physiological and other signal data, obtained from a vascular region, and other tissues of a subject. In some applications, data acquisition of the various signals may be performed simultaneously, or synchronously. For example, DCS data may be acquired concurrently, or at approximately the same sampling rate, as ECG data. However, this need not be the case. For example, DCS data may be acquired at 100 Hz while the ECG data is acquired at a much higher frequency. Also, various measurements may be made once, intermittently, periodically, or continuously.

In some aspects, the optical processing system 106 in cooperation with the controller 110, and methods of operation of the present disclosure may be capable of acquiring and processing multiple measurements per second to, thereby, achieve a speed, or temporal resolution, to determine pulsatile information and create accurate measures not achieved or recognized in non-invasive systems previously. In some aspects, data may be acquired a temporal resolution greater than a pulsatile frequency of cerebral and other blood flow in a the subject. As an example, DCS data, may be sampled at frequencies of up to 500 Hz, although higher frequencies may be possible. Such pulsatile DCS (pDCS) data stands in contrast to traditional DCS systems and methods that, for example, have a sampling time for DCS measurements of approximately 1.5 seconds or longer. Other data may also be acquired at frequencies or sampling rates consistent with providing pulsatile information.

Figure 2:
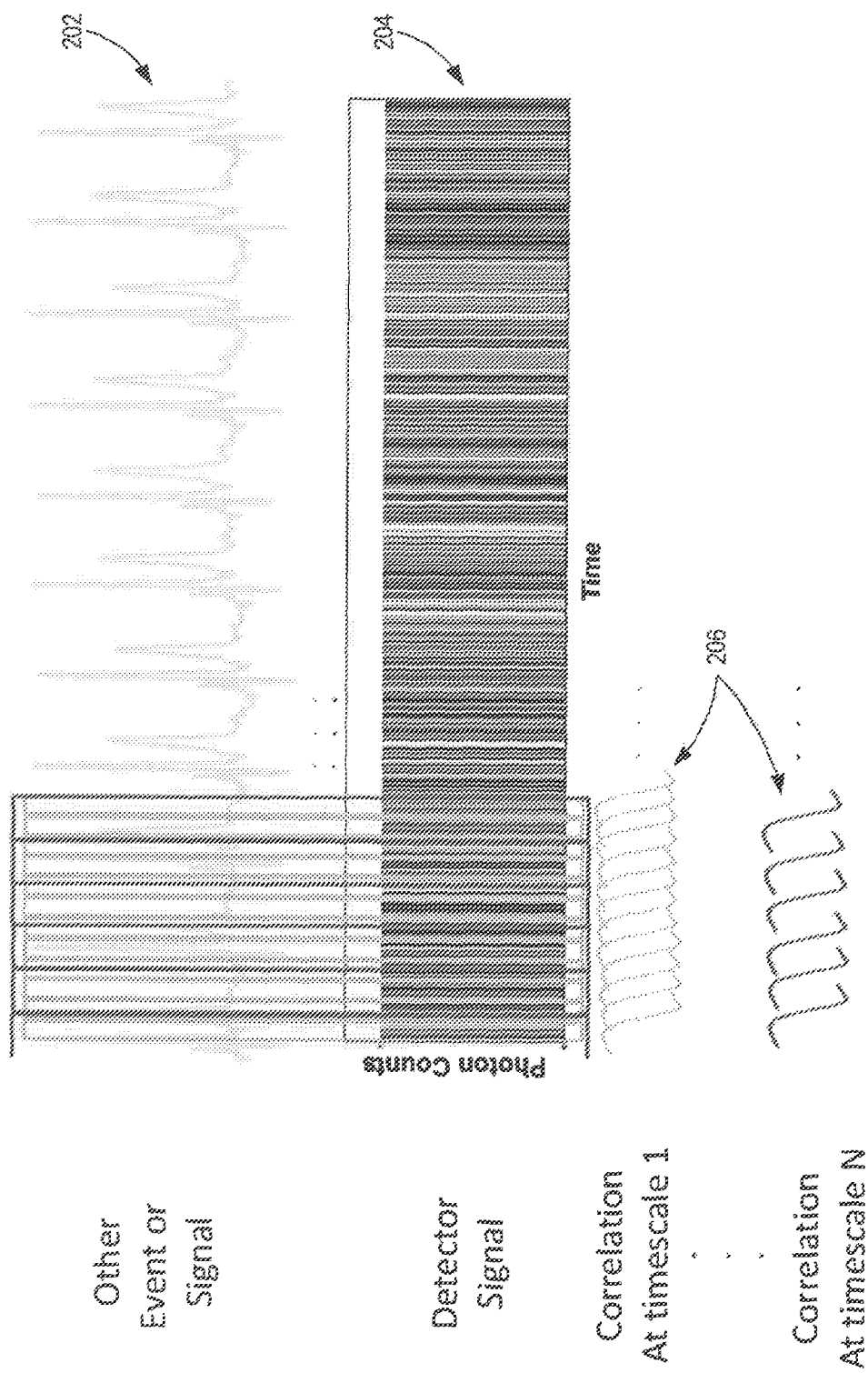
FIG. 2 is a graphical illustration showing acquisition, gating and average of photon count data, in accordance with aspects of the present disclosure.

The controller 110 may be configured to utilize measured signals to construct various time series waveforms. For example, FIG. 2 shows acquisition of ECG data 202 and DCS data 204 as a function of time. The controller 110 may also be configured to assemble acquired signals into a frequency representation, as power spectra. As such, the controller 110 may be configured to apply a Fast Fourier Transform (FFT), for example, to the acquired signals. Other signal representations may also be generated by the controller 110, including signal derivatives, differentials, differences, and so forth. The controller 110 may also determine signal amplitudes, timing, phases, correlations, and so forth. Processing of signals by the controller 110 may be performed in real-time, near real-time, or by post-processing, either in the time or frequency domain or both. In addition, the controller 110 may be configured to up-sample, down-sample, differentiate, integrate, average, scale, amply, filter, and so forth, various measured signals.

In some aspects, the controller 110 may combine DCS data acquired over a number of cycles, the DCS data being acquired at specific time points or over a range of time points in the cardiac cycle. Individual measurements may or may not have sufficient signal to noise ratio (SNR) for analysis. As such, a measurement taken from one cardiac cycle can be averaged with a measurement from a different cardiac cycle, while ensuring proper gating of the signals. That is, individual measurements could be timed to exactly coincide with the same portion of the cardiac cycle, or the measurements could be asynchronous to the cycle resulting in an equivalent time average. Equivalent time averaging has superior sampling of the cycle, but either method can be used. In addition to the cycle average, the same data can be averaged over longer times. In this manner, both pulsatile blood flow, average blood flow, and absolute blood flow may be computed. Alternatively, or additionally, the controller 110 may integrate or combine data acquired over an entire cardiac cycle.

In some aspects, the controller 110 of FIG. 1 may be configured to generate, by way of the correlator 118, correlation curves using acquired DCS data, and more specifically pDCS data. In this manner, various desirable parameters, blood flow, and more specifically absolute blood flow, may be determined, as will be described. In particular, the correlator 118 may receive photon count data from the detector module 114 and calculate intensity autocorrelation functions at various time scales using the photon count data. Although the correlator 118 is shown in FIG. 1 as separate from the controller 110, it may be readily appreciated that these could be integrated into one system. For instance, the controller 110 may include various hardware and software for directly calculating intensity autocorrelation functions.

Referring again to FIG. 2, correlation curves 204, obtained at different time scales using DCS data, are shown. Such correlation curves may be generated either synchronously or asynchronously along with other acquired measurements, such as ECG and other physiological measurements. For example, DCS measurements may be collected at multiple time points within a cardiac cycle measured using ECG data, for instance.

The controller 110 may be further configured to analyze acquired data, including optical data and physiological data, in order to provide estimates of quantities, such as pulsatile blood flow, blood inflow, blood outflow, absolute blood flow, and others, as will described. For instance, the controller 110 may be configured to analyze autocorrelation curves generated at various timescales to determine pulsatile blood flow associated with one more points in a cardiac cycle.

In accordance with the present disclosure, the controller 110 may be configured to utilize blood flow measurements with NIRS or oximetry measurements to determine an absolute blood flow, such as an absolute cerebral blood flow. As such, the controller 110 may be programmed to estimate a change in total hemoglobin concentration from acquired DCS data, and use the change in total hemoglobin concentration to determine the blood volume. Using blood flow and blood volume, a blood inflow and blood outflow may be determined, from which absolute blood flow is computed. In some aspects, the controller 110 may be configured to integrate an absolute value of a first derivative or a second derivative of the blood outflow. The controller 110 may also be programmed to determine a phase, or phase difference, between a determined blood inflow and blood outflow.

In some aspects, the controller 110 may be programmed to determine a phase difference between various computed quantities, including an index of blood flow, a blood volume, a blood inflow, a blood outflow, a derivative of blood volume, an integral of blood volume, a derivative of the index of blood flow, an integral of the index of blood flow, or combinations thereof. For example, the controller 110 may be programmed to determine a phase difference between a cerebral blood volume (CBV) and an index of cerebral blood flow (CBFi), or between dCBV/dt, or derivative of CBV, and CBFi, or between CBV and an integral CBFi, and other combinations.

The controller 110 may be further configured to determine a condition of the subject based on determined quantities, such as absolute blood flow, and others. For example, the controller 110 may be configured to determine a risk of cerebral ischemia, blood clots, or a loss of autoregulation and/or regulatory reserve, and so forth. In addition, the controller 110 may also be configured to determine an effectiveness of an administered treatment using determined, including absolute blood flow.

In some embodiments, the system 100 may also include capabilities for generating optical data using ultrasonic tagged light. Specifically, the system 100 may include one or more ultrasound probes or ultrasound sensors (not shown in FIG. 1) configured to module light waves, produced using the source module 112 or another source, using various ultrasound frequencies. Such ultrasound probes or sensors may be included in the optical processing system 106 or may be a separate system. As such, the optical processing system 106 and controller 110 may be configured to generate optical data by detecting ultrasonic tagged light in accordance with applied ultrasound frequencies.

The controller 110 may be further configured to generate and provide a report to a user. The report may include a variety of information including, real-time or intermittent physiological signals or measured quantities, such as absolute blood flow, blood inflow, blood outflow, as well as other clinically relevant parameters, including cerebral perfusion pressure (CPP), cerebrovascular resistance (CVR), vessel wall tone, cerebral blood flow-cerebral spinal fluid pulsatility coupling and cerebral compliance, dynamic autoregulation, cerebral perfusion reserve, and other parameters or quantities generated therefrom. Provided signals may be in the time domain, as time series, as well as the frequency domain, as power spectra.

The report may also indicate a condition of the subject being monitored, as well as other information associated with the subject. For instance, the report may indicate a risk for a cerebral ischemia, blood clots, or a loss of autoregulation or regulatory reserve. The report may further include an audio and/or visual alarm to indicate an acute condition, such as when one or more estimated quantities exceed a safe threshold, or a risk for complications is increased. For example, an alarm may be provided when an absolute cerebral blood flow exceeds or drops below a threshold value.

In accordance with aspects of the present disclosure, pDCS measurements may be combined or correlated with NIRS or cerebral oximetry measurements to obtain absolute blood flow. In particular, NIRS or cerebral oxymetry measurements can provide valuable information about changes in cerebral hemoglobin concentrations and changes in cerebral blood volume (CBV). Changes in CBV are usually proportional to changes in total hemoglobin concentration ([$Hb_T$]), which can be a proxy measure for CBV. Other NIRS measures, such as $\Delta[Hb_T]$, [$Hb_O$], and so forth are also usable as proxies for CBV with varying degrees of accuracy.

Absolute cerebral blood flow, referred to hereafter as CBF, and CBV are related to blood inflow and blood outflow of a vascular network or vascular cerebral region through complementary ways. In this context, the blood inflow is usually arterial blood and blood outflow is usually venous return. As described, discussion that follows is not limited to cerebral blood flow, and may readily be generalized to other organs or tissues in a subject's anatomy.

In one example, CBF may written to be proportional to a sum of blood inflow and blood outflow, as follows:

$$CBF = \frac{1}{2}(Flow_{In} + Flow_{Out}) \qquad (1)$$

However, more generally, CBF can be described by any weighted sum of $Flow_{In}$ and $Flow_{Out}$.

The derivative of CBV, or its proxies, are proportional to the difference of inflow and outflow:

$$\frac{d(CBV)}{dt} = Flow_{In} - Flow_{Out} \qquad (2)$$

Given measurements of CBF and CBV, Eqns. 1 and 2 can be used to estimate $Flow_{in}$ and $Flow_{out}$, and hence absolute cerebral blood flow, as detailed below.

As mentioned, DCS measures an index of cerebral blood flow ($CBF_i$), which, for example, can be described as being proportional to absolute cerebral blood flow according to:

$$CBF = a\ CBF_i, \qquad (3)$$

where 'a' is a calibration constant. In other aspects, more general relationships can relate $CBF_i$ and CBF. CBV can be estimated from NIRS hemoglobin measurements given, for instance, the hemoglobin content of the blood or the hematocrit. Thus the following equations are obtained for the specific examples above, $$Flow_{In} = \frac{2}{3}\left(\frac{d(CBV)}{dt} + aCBF_i\right) \qquad (4)$$

$$Flow_{Out} = \frac{2}{3}\left(-\frac{d(CBV)}{dt} + aCBF_i\right). \qquad (5)$$

Equations 4 and 5 can be used to estimate the $Flow_{in}$ and $Flow_{out}$ during a cardiac cycle. The estimation of $Flow_{in}$ and $Flow_{out}$ depends on the $CBF_i$ calibration constant 'a'.

Various constraints may be used to obtain a reasonable estimate of 'a', such constraints being intended to mimic physiological conditions. For instance, $Flow_{out}$ and $Flow_{in}$ may be constrained to not become negative during the cardiac cycle. Also, $Flow_{out}$ may be constrained to be flat, namely:

$$\frac{d^2(Flow_{out})}{dt^2} \approx 0 \qquad (6)$$

which places a lower limit on the value of 'a'. The value of 'a' may be further constrained by the limits on the magnitude of non-pulsatile flow. Specifically, an upper limit for 'a' may be obtained by not permitting CBF to become larger than a physiological reasonable value. Note that in the case of a non-pulsatile outflow, the outflow is identically equal to:

$$Flow_{Out} = \langle Flow_{in}\rangle_{cardiac\ cycle} \qquad (7)$$

the time average of inflow over the cardiac cycle plus potentially a trivial term accounting for any steady-state changes in average CBV.

With the assumption of non-pulsatile outflow, 'a' can then be algebraically determined from the observed values of CBF and $CBF_i$.

$$Flow_{Out} = \langle Flow_{in}\rangle_{cardiac\ cycle} \qquad (7)$$

It is also possible to determine 'a' independently through measurements by other CBF measurement modalities, such as bolus tracking of fluoresence indicators, arterial spin labeling, Xe clearance, and so forth.

When CBF changes arise, a practically important question is whether CBF changed due to changes in arterial supply or due to restriction of venous return. The inflows and outflows have diagnostic utility since they are representative of the resistance to blood flow of different parts of the cerebral vascular network. Inflows and inflow resistance are dominated by vasomotor tone of cerebral resistance vessels, functional hyperemia, and autoregulation. Outflows and outflow resistance are dominated by venous resistance and are sensitive to compression. Generally $F_{in}(t) \neq F_{out}(t)$, however:

$$\oint_{cardiac\ cycle} = (F_{in}(t) - F_{out}(t))dt = \Delta CBV \qquad (9)$$

If there is no net change in CBV, then $\Delta CBV=0$ and the first moments are equal:

$$\langle Flow_{out}\rangle_{cardiac\ cycle} = \langle Flow_{in}\rangle_{cardiac\ cycle} \qquad (10)$$

If $\Delta CBV \neq 0$, then there is simply an addition of a trivial term to account for the net change. Thus, changes to the inflows and outflows are related to changes in the shape of their curves. Specifically, since the pulse amplitude in CBV is dominated by arterial inflow resistance, changes in arterial inflow resistance will change the inflow pulse amplitude. Changes in venous resistance will affect the phase between the pulsatile peaks inflow and outflow.

The phase between $Flow_{in}$ and $Flow_{out}$ can be preserved regardless of value of 'a'. Consequently, the phase difference can be determined absolutely without performing an estimation of 'a'. Phase monitoring is especially advantageous in hydrocephalus and venous return pathologies. Flow amplitude trends may be monitored if 'a' is not estimated or measured absolute if 'a' is determined by one of the means above.

As appreciated from the above, the present disclosure provides a substantial improvement over previous technologies by providing a novel approach for non-invasively monitoring absolute blood pressure. In previous brain monitoring techniques, only inflows were measured and the measurements could only be performed on large arteries which act to feed many brain regions. In contrast, the present approach utilizes pDCS to measure both inflow and outflow in the microvasculature of localized regional tissues. Furthermore, pDCS can be combined with other hemodynamic measures, for example spectroscopic measurements of CBV, which are also related to inflow and outflow, in the microvasculature of the same localized region.

In addition, prior to this disclosure, dynamic venous outflows in the brain were very difficult to measure since the collector veins most accessible were the sub-arachnoid veins. These veins are very close to the entry into the dural sinuses, which are large venous reservoirs which buffer flow and attenuate the outflow profile. pDCS alone and/or in combination with NIRS or other modalities, as described herein, enable non-invasive determination of inflow and outflow at the localized tissue level where inflows and outflows are un-attenuated and closely reflect regional physiology.

Figure 3:
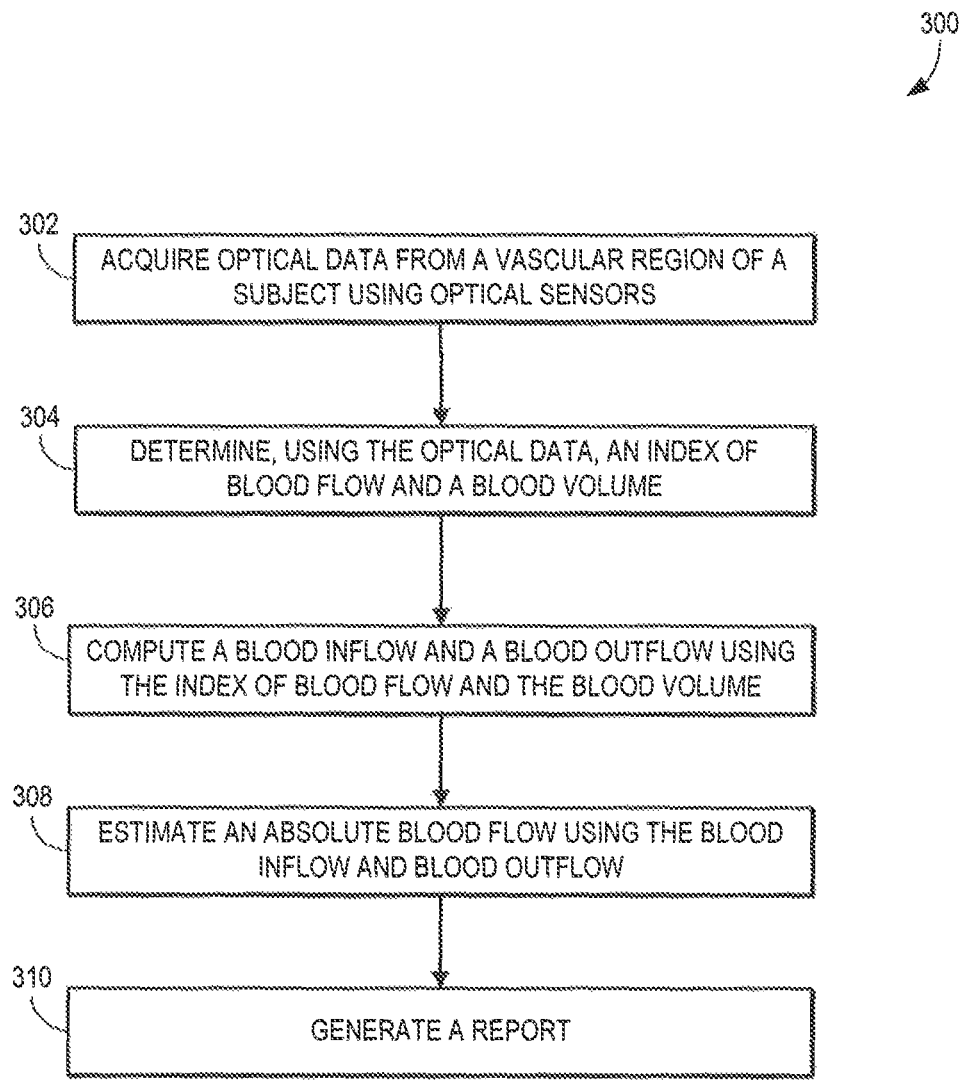
FIG. 3 is a flowchart setting forth steps of a process in accordance with aspects of the present disclosure.

Referring now to FIG. 3, the steps of a process 300 in accordance with aspects of the present disclosure are described. The process 300 may be carried out on any system or apparatus, such as the one described with reference to FIG. 1. As shown in FIG. 3, the process 300 may begin at process block 302 with acquiring optical data associated with one or more vascular regions or tissues, by using various sensors placed about a subject. In some aspects, optical data associated with a subject's brain is acquired at process block 302.

In general, optical data described herein may refer to raw data obtained using optical sensors, in the form of photon data, such as photon count data, photon timing data, photon intensity data, and the like. In addition, optical data may also refer to processed data, such as correlation data. Example optical data may generally include DCS data, and NIRS data. In some aspects, optical data may also include ultrasound tagged light data.

Other data, including physiological data, may also be acquired at process block 302. Example physiological signal data may include ECG data, EEG data, blood pressure data, respiratory data, hemoglobin data, pulse oxymetry data, and other data. As described, to acquire the data, one or more sensors may be placed at various locations about a subject, including the skull, forehead, neck, arms, hands, fingers, torso, chest, legs, feet, toes, and so forth.

The data obtained at process blocks 302 may be acquired in any number of ways, as described, including intermittently, continuously, synchronously or asynchronously. In some aspects, DCS data, and other data, may be acquired or sampled using temporal resolution greater than a pulsatile frequency of a cardiac cycle. In this manner, pDCS may be acquired, for instance. Data may also be acquired over multiple cardiac cycles.

The acquired data may also be processed at process block 302. For instance, depending upon the requisite signal to noise ratio (SNR), data acquired over a number of cardiac cycles may be combined, for instance by averaging or integrating. For instance, photon data, whether a simple number of counts per time interval or the number of time intervals between photon detection, can be processed and averaged for cycles and events. For example, the photon count data obtained over short periods within a cardiac cycle can be used to calculate correlation curves and perform cycle averaging. The same photon count data can be used with other data over a longer time to calculate correlation curves on different time scale or period of interest (e.g. steady-state average, respiration, etc.). This approach can be used for non-cyclical events as well. For example, the blood flow associated with periods of time before and after a distinct EEG event such as a burst or seizure. In some aspects, gating and averaging can be performed prospectively and/or retrospectively.

Then, at process block 304, acquired optical data may be used to determine an index of blood flow. Advantageously, pulsatile data, such as pDCS, is utilized to determined the index of blood flow. As such, each determined index of blood flow is representative of a time point in a cardiac cycle. Alternatively, a determined index of blood flow is associated with a time period in the cardiac cycle, or a time point or time period from multiple cardiac cycles. As described, determining the index of blood flow includes utilizing photon data from various time scales to generate an autocorrelation function, which is then fit to a correlation transport model to extract the index of blood flow.

As indicated by process block 304, a blood volume, and more specifically a change in blood volume, may also be determined. Specifically, using the photon intensity changes measured using DCS or NIRS sensors, total hemoglobin concentration changes during the cardiac cycle may be estimated. Measurement of blood hemoglobin concentration may then be used to convert hemoglobin concentration changes during cardiac cycle to blood volume changes during cardiac cycle.

Then, a blood inflow and a blood outflow may be computed using the determined index of blood flow and blood flow volume. As described, Eqns. 4 and 5 may be solved to determine blood inflow and blood outflow. The value of the calibration constant 'a' in the above equations may be determined using various constraints, such as assumptions about the flatness of blood outflow, or assumptions about the blood flow values. Specifically, the flatness of blood outflow may be quantified by simply considering the difference between the maximum and minus value of blood outflow and minimizing this difference. An absolute value of the first or second derivate of outflow may also be integrated and the value minimized. However a flatness of blood outflow need not be assumed. For instance, blood outflow may be more pulsatile, but a constraint on total flow, or absolute blood flow may be placed. For instance, an absolute blood flow may be smaller than a threshold or maximum physiologically relevant blood flow value.

As indicated by process block 308, the determined blood inflow and blood outflow may then be used to estimate absolute blood flow, in accordance with Eqn. 1. In some aspects, the determined absolute blood flow may be correlated with raw or processed physiological data, such as ECG data, EEG data, blood pressure data, respiratory data, hemoglobin data, pulse oxymetry data, and other data. As such, other parameters may also be estimated at process block 310 using the acquired optical data and physiological data. For example, cerebral perfusion pressure, vessel wall tone, cerebral blood flow-cerebral spinal fluid pulsatility coupling, cerebral compliance, dynamic autoregulation, cerebral perfusion reserve, cerebrovascular resistance, oxygen saturation, hemoglobin concentration, cardiac output, stroke volume, brain activity, cardiac activity, and various combinations or changes thereof, may be determined at process block 308 and correlated with absolute blood flow.

In some aspects, a condition of the subject based on determined parameters, such as absolute blood flow, and others, may be determined at process block 308. For example, a risk of cerebral ischemia, or a loss of autoregulation and/or regulatory reserve may be determined. In other aspects, an effectiveness of an administered treatment may be determined using determined physiological parameters, including absolute blood flow. Such determinations may be made by comparing computed parameters with a baseline, reference or database.

Then, at process block 310 a report, of any form, may be generated and provided to a user. The report may include a variety of information including, real-time or intermittent values of measured physiological parameters or quantities, such as absolute blood flow, blood inflow, blood outflow as well as other clinically relevant parameters, including EEG, ECG, hemoglobin concentrations, changes thereof, and other parameters or quantities generated therefrom. The report may also identify a condition of the subject being monitored, as well as other information associated with subject. For instance, the report may indicate a risk for a cerebral ischemia, or a loss of autoregulation or regulatory reserve. The report may further include an audio and/or visual alarm to indicate an acute condition, such as when one or more estimated quantities exceed a safe threshold, or a risk for complications is increased. For example, an alarm may be provided when an absolute cerebral blood flow exceeds or drops below a threshold value.

Process blocks 302 through 310 may be carried out once, or repeated, either intermittently, or continuously, as desired.

As described, FIG. 2 shows an example of how the photon counts can be correlated in reference to another signal or event at one or more timescales. Specifically, FIG. 2 shows ECG data 202 and DCS data 204 as a function of time. In particular, the DCS data 204, in the form of a stream of photon counts, can be parsed, in either synchronous, partially synchronous, or asynchronous manner, with regards to another physiological signal, such as ECG data 202, to generate one or more correlations functions 206. Such parsing may be achieved with reference to other physiological signals, including ECG, EEG, NIRS, or other physiological signals. Thus, the same data could be combined with regards to multiple events with the appropriate time and duration for each signal. For example, the same signal could process blood flow with regards to cardiac cycle from an ECG and flow before and after a seizure event recorded in EEG. Different time scales could be used between different signals or within the same signal, including, but not limited to, determining both pulsatile and steady flow.

In some aspects, intra-cardiac cycle and intra-respiratory cycle flows, gated by appropriate cardiac and respiratory signals, may be calculated at two different timescales within the ECG. In others, cardiac cycle timing could be determined from a blood pressure sensor or the optical signals themselves. The timing and duration could be fixed or dynamically and/or algorithmically determined, either in real-time, near-real time, or in post-processing. For example, the DCS data 204 could be parsed on a cycle-by-cycle basis, following the spontaneous changes in heart rhythm. The processing may include other transformations, for example a temporal offset to account for the difference in phase between an ECG signal and the CBF signal to account for the transit time of blood from the heart to the brain. The processing could be performed either in software (for example, using FFTs, etc.), in hardware (for example, multi-tau algorithm, FFT, etc.), or any combination thereof.

Figure 4:
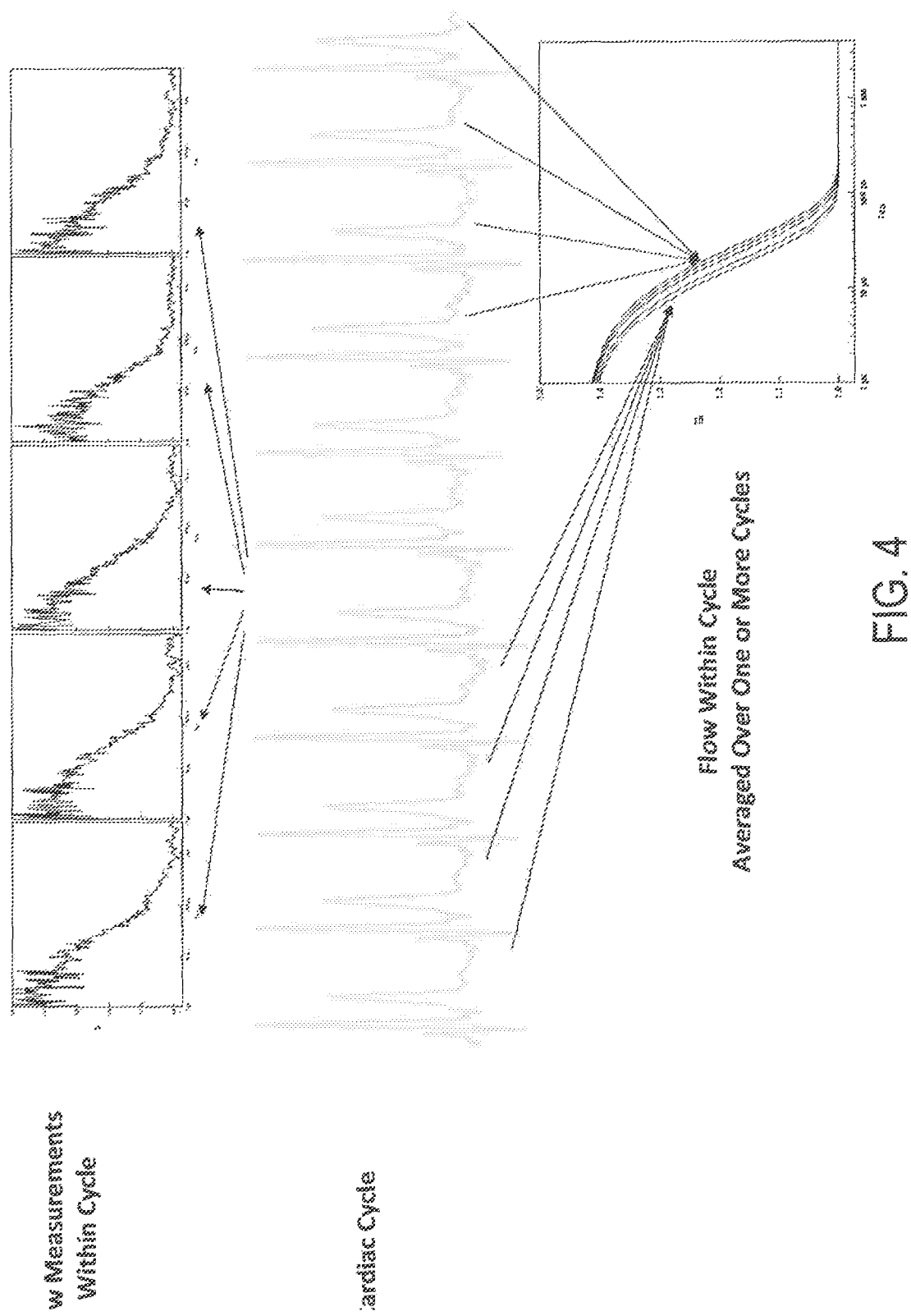
FIG. 4 is a graphical illustration showing acquisition, gating, and averaging of pulsatile diffuse correlation spectroscopy (pDCS) data.

By way of example, FIG. 4 shows pulsatile blood flow measurements obtained from a human subject in accordance with aspects of the present disclosure. In this example, flow measurements were acquired in an integration time less than the period of a cardiac cycle with a hardware correlator, as described with reference to FIG. 1. As described, in some aspects, flow measurements may be inter-cycle combined, processed, and/or averaged with equivalent intra-cycle measurements. In this manner, the signal-to-noise ratio and/or intra-cycle time resolution may be increased. The amount of combination can be set by a predetermined amount, such as time, number of samples and so forth, or determined dynamically and/or algorithmically, such as (SNR, number of intracycle points, etc.). Measurements may also be combined, processed, and/or averaged with or without regard to the cycle for the determination of baseline, steady, etc. flow or flows.

Figure 5A:
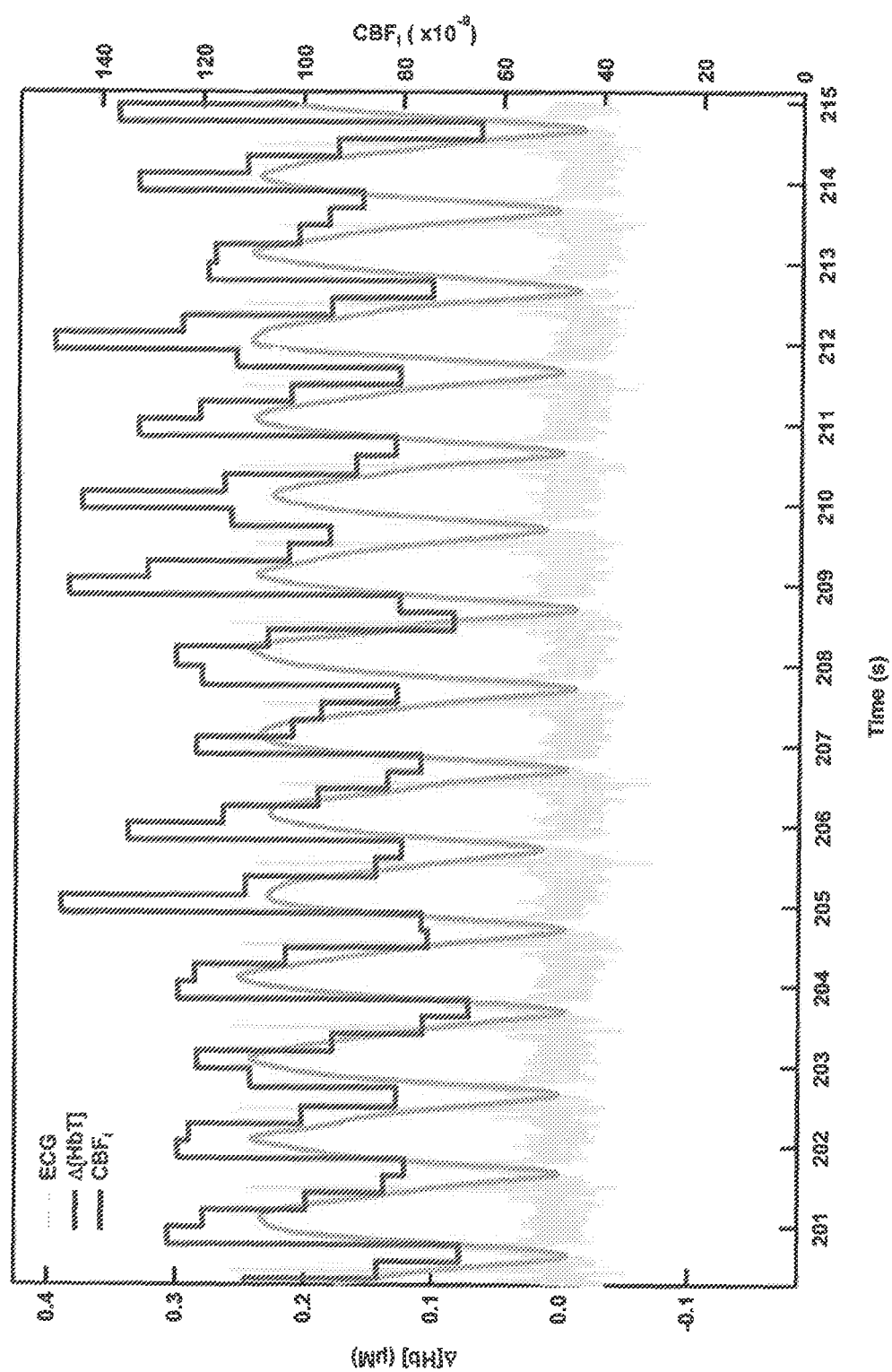
FIG. 5A is a graph showing simultaneous electrocardiograph (ECG), near infrared spectroscopy (NIRS) and pulsatile DCS data.
Figure 5B:
FIG. 5B is another graph showing simultaneous ECG, NIRS and pDCS data.

By way of yet another example, FIGS. 5A and 5B demonstrates simultaneous measurements of pulsatile DCS with ECG and continuous wave (CW) NIRS. As can be seen, the index of cerebral blood flow (CBFi) signal has a resolution of 4-5 samples per second. The NIRS and DCS data were collected from an integrated optical probe placed on the forehead to sample the same tissue in the cortex. ECG was recorded from two leads placed on the chest of the subject. Although the data points are acquired asynchronously, the pulsatile blood flow, hemoglobin concentration changes and cardiac electrical activity were all physiologically synchronous. However, due to transit time differences between the heart beat and arrival of blood in the cortex, there was a phase difference between the ECG/NIRS signals and the ECG activity. In general, such phase difference can be accounted for by calibration and/or processing.

Figure 5C:
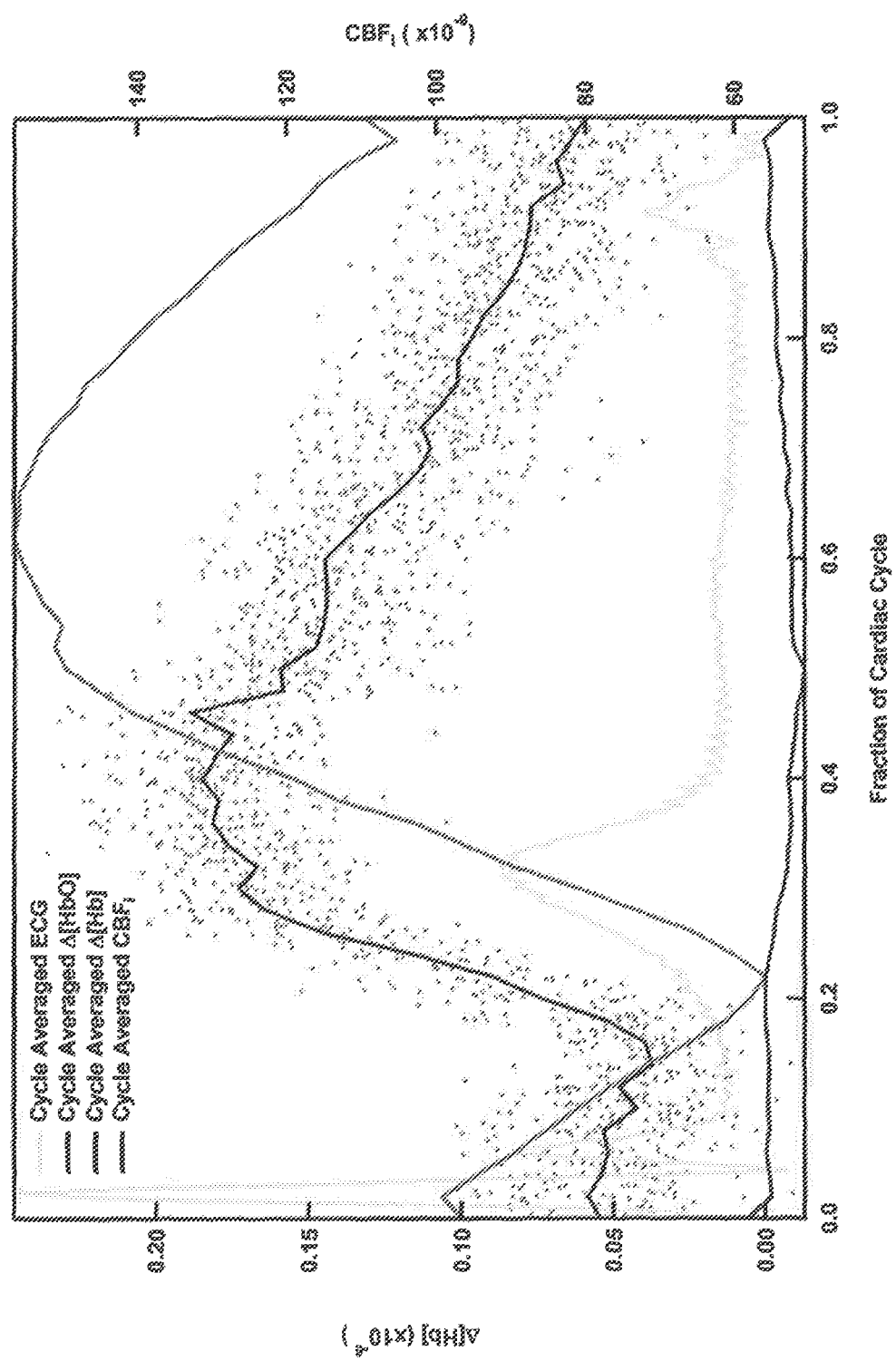
FIG. 5C is graph showing asynchronous cardiac cycle averaging.

By yet another example, FIG. 5C the results of cycle averaging. Further processing can be performed to perform calibrations and/or extract relevant parameters from the data. Specifically, a portion of the signals from FIGS. 5A and 5B was averaged over the cardiac cycle in an equivalent time average.

Figure 6A:
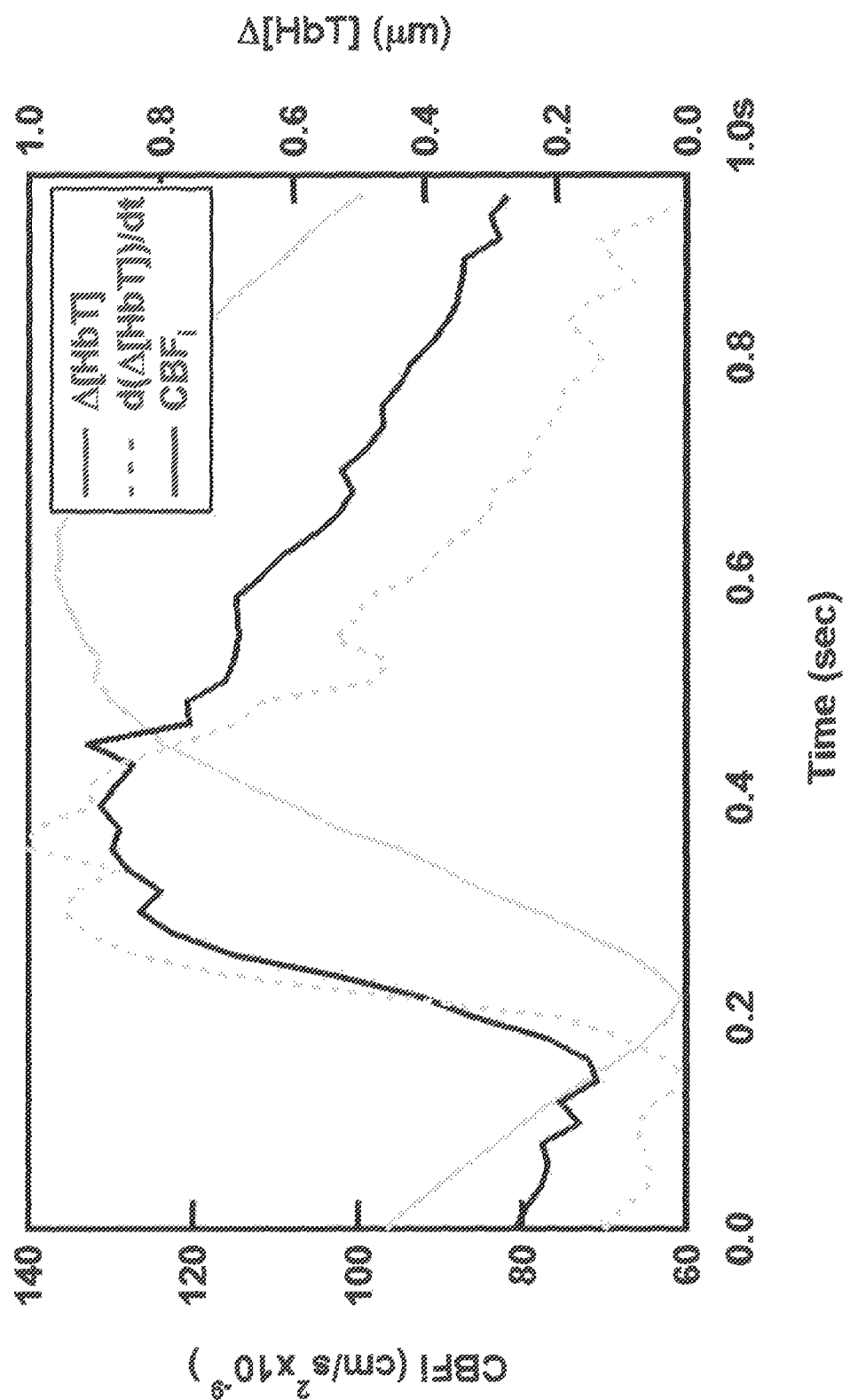
FIG. 6A is a graph showing measurement of both pDCS and NIRS for estimating blood inflow and outflow.
Figure 6B:
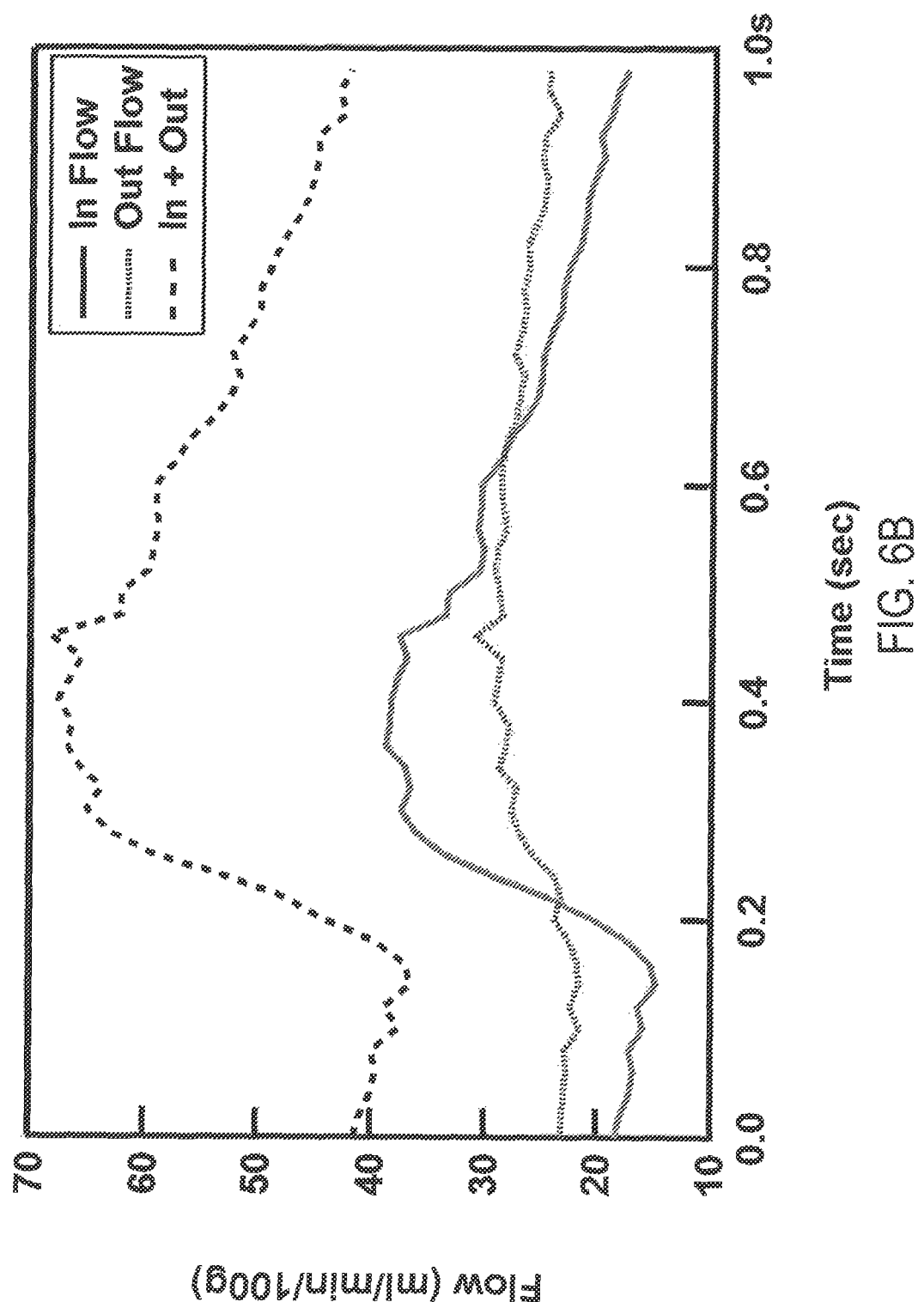
FIG. 6B is another graph showing measurement of both pDCS and NIRS for estimating blood inflow and outflow.

As further examples, FIGS. 6A and 6B demonstrate the measurement of both pDCS and NIRS, and calculation of blood inflow and blood outflow, respectively, in accordance with aspects of the present disclosure. Specifically, FIG. 6A shows time series of index of cerebral blood flow obtained from pDCS data, and change in total hemoglobin concentration, and derivative of the change in total hemoglobin concentration obtained from NIRS data. Using acquired data absolute blood flow was determined, including blood inflow and blood outflow, as shown in FIG. 6B. Specifically, the NIRS measurement of hemoglobin concentration was the integral of the difference between inflow and outflow. Differentiating the NIRS measurements resulted in the difference between inflow and outflow. As described, these were solved for the inflow and outflow. Expectedly, the inflow exhibited a strong pulsatile component during the cardiac cycle while the outflow was lower in magnitude and broader.

As appreciated from FIGS. 6A and 6B the index of cerebral blood flow, shown in units of $cm/s^2$, is utilized to obtain absolute blood flow, which is in units mL/min/100 g. Such calibrated cerebral blood flow is more intuitive and hence clinically more relevant, allowing direct comparison with population data, for instance. For instance, the mean value of the absolute blood flow shown in FIG. 6B is about 51 ml/min/100 g of tissue, which agrees with typical values for adult human values of cerebral blood flow measured using more invasive techniques.

In summary, the present disclosure overcomes the drawbacks of previous technologies by providing a system and method for accurately and non-invasively monitoring patients continuously, including monitoring absolute blood flow for different vascular regions. More specifically, the system and method described herein utilize optical and physiological data to determine parameters useful in the diagnosis and management of patients.

As may be appreciated from descriptions herein, the present disclosure provides a wide range of applicability. For example, the system and method described can be used to monitor changes in blood flow, and autoregulation capacity with drugs or anesthetics, as well as provide monitoring and/or diagnostics with pharmacological manipulations include bolus testing. In addition, the present system and method may be applied to monitoring vasospasm or the effect of vasospasm or vasoparalysis, as well as monitoring cortical spreading depression or the effect of cortical spreading depression. The present system and method may also be applied to monitoring hemorrhages, including subarachnoid hemorrhages, and post-hemorrhage monitoring, tumors, hematoma, hydrocephalus, edema, vascular engorgement, hypercapnia, hypoxia, shock, sepsis. Furthermore, the present approach may be used to investigate chronic diseases and conditions such as hypertension, sleep and other apneas, etc. (measurement of pathological chronic changes in vascular tone), as well as hydrocephalus.

The present system and method may be applied to monitor congestive heart failure, blood flow in non-cerebral organs, peripheral vascular disease. In addition, the provided system and method may be utilized in perioperative, intensive and critical care, as well as goal-directed blood pressure support in patients with critical carotid artery stenosis. Furthermore, the present system and method may be utilized in perioperative management of patients undergoing carotid endarterectomy, and in patients with cardiopulmonary bypass, as well as optimization of blood pressure management in patients with traumatic brain injury undergoing neurosurgical or non-neurosurgical procedures.

The present system and method may be further utilized to provide physiological parameters and information useful for the diagnosis and management of patients under a variety clinical situations, including but not limited to, critical care, such as infant, pediatric, or neuro intensive care units, anesthesia and/or surgery, emergency and trauma wards, recovery wards, post intensive care, battle fields, spacecrafts, extreme environments, during sports or on the sidelines, disaster or accident sites, and so forth.

The present invention has been described in terms of one or more preferred embodiments, and it should be appreciated that many equivalents, alternatives, variations, and modifications, aside from those expressly stated, are possible and within the scope of the invention.

The invention claimed is:

1. A system for non-invasively estimating an absolute blood flow of a vascular region in a subject using optical data, the system comprising:
    an optical coupling system comprising a source probe and a detector probe configured to transmit to and receive light signals from one or more locations about a subject,
        the source probe and the detector probe comprising a diffuse correlation spectroscopy (DCS) sensor;
    an optical processing system comprising a detector configured to generate optical data using received light signals,
    the optical data comprising DCS measurements having a temporal resolution of at least 25 Hz;
    a computer programmed to:
        receive from the optical processing system optical data associated with a vascular region;
        determine, using the optical data, an index of blood flow and a blood volume;
        estimate an absolute blood flow using the index of blood flow and the blood volume; and
        generate a report indicative of the absolute blood flow of the vascular region.

2. The system of claim 1, wherein the vascular region comprises a cerebral region.

3. The system of claim 1, wherein the sensor of the optical coupling system further comprises near infrared spectroscopy (NIRS) sensors.

4. The system of claim 1, wherein the optical processing system is further configured to generate near infrared spectroscopy (NIRS) data, ultrasound tagged light data, or a combination thereof.

5. The system of claim 1, wherein the computer is further programmed to estimate a change in total hemoglobin concentration using the optical data.

6. The system of claim 5, wherein the computer is further programmed to use the change in total hemoglobin concentration to determine a change in blood volume.

7. The system of claim 1, wherein the computer is further programmed to compute a blood inflow and a blood outflow using the index of blood flow and a change in blood volume.

8. The system of claim 7, wherein the computer is further programmed to integrate an absolute value of a first derivative or a second derivative of the blood outflow.

9. The system of claim 7, wherein the computer is further programmed to determine a phase between the blood inflow and blood outflow.

10. The system of claim 1, wherein the computer is further programmed to determine a condition of the subject based on the absolute blood flow.

11. The system of claim 7, wherein the computer is further programmed to determine a phase difference between the index of blood flow, the blood volume, the blood inflow, the blood outflow, a derivative of blood volume, an integral of blood volume, a derivative of the index of blood flow, an integral of the index of blood flow, or a combination thereof.

12. The system of claim 1, wherein the absolute blood flow is expressed in units corresponding to volume/time/mass.

13. A method for non-invasively estimating an absolute blood flow of a vascular region in a subject using optical data, the method comprising:
    a) acquiring optical data from the vascular region using one or more optical sensors placed about the subject, the optical sensors comprising a diffuse correlation spectroscopy (DCS) sensor, and
        the optical data comprising DCS measurements having a temporal resolution of at least 25 Hz;
    b) determining, using the optical data, an index of blood flow and a blood volume associated with the vascular region;
    c) computing a blood inflow and a blood outflow using the index of blood flow and the blood volume;
    d) estimating an absolute blood flow using the blood inflow and blood outflow computed at step c); and
    e) generating a report indicative of the absolute blood flow of the vascular region.

14. The method of claim 13, wherein the vascular region comprises a cerebral region.

15. The method of claim 13, wherein optical data further comprises near infrared spectroscopy (NIRS) data.

16. The method of claim 13, wherein the method further comprises using the optical data to estimate a change in total hemoglobin concentration.

17. The method of claim 16, wherein the method further comprises using the change in total hemoglobin concentration to determine a change in blood volume.

18. The method of claim 13, where in the method further comprises integrating an absolute value of a first derivative or a second derivative of the blood outflow.

19. The method of claim 13, wherein the method further comprises determining a phase between the blood inflow and blood outflow.

20. The method of claim 13, wherein the method further comprises acquiring physiological data from the subject using one or more physiological sensors placed about the subject.

21. The method of claim 20, wherein the physiological data comprises at least one of electrocardiogram (ECG) data, electroencephalogram (EEG) data, blood pressure data, respiratory data, hemoglobin data, pulse oxymetry data, or a combination thereof.

22. The method of claim 13, wherein the method further comprises controlling an optical processing system to generate optical data using an integration time less than a period of a cardiac cycle.

23. The method of claim 13, wherein the method further comprises determining an effectiveness of an administered treatment using the absolute blood flow.

24. The method of claim 13, wherein the method further comprises determining a condition of the subject based on the absolute blood flow.

25. The method of claim 13, wherein the method further comprises determining a phase difference between the index of blood flow, the blood volume, the blood inflow, the blood outflow, a derivative of blood volume, an integral of blood volume, a derivative of the index of blood flow, an integral of the index of blood flow, or a combination thereof.

* * * * *